United States Patent [19]
Martinelli et al.

[11] Patent Number: 5,800,994
[45] Date of Patent: Sep. 1, 1998

[54] HYBRIDIZATION-LIGATION ASSAYS FOR THE DETECTION OF SPECIFIC NUCLEIC ACID SEQUENCES

[75] Inventors: Richard A. Martinelli, Brighton; John C. Arruda, Attleboro, both of Mass.

[73] Assignee: Chiron Diagnostics Corporation, East Walpole, Mass.

[21] Appl. No.: 685,793

[22] Filed: Jul. 24, 1996

Related U.S. Application Data

[63] Continuation of Ser. No. 222,613, Apr. 4, 1994, abandoned.

[51] Int. Cl.$^6$ .................. C12Q 1/68; C12Q 1/70; C12P 19/34; C07H 21/04
[52] U.S. Cl. .................. 435/6; 435/5; 435/4; 435/91.2; 536/24.3; 536/24.33; 536/24.36
[58] Field of Search ................ 435/6, 4, 5, 91.2; 536/24.3, 24.33, 24.36

[56] References Cited

U.S. PATENT DOCUMENTS

| | | | |
|---|---|---|---|
| 4,486,539 | 12/1984 | Ranki | 436/504 |
| 4,563,419 | 1/1986 | Ranki | 435/6 |
| 4,883,750 | 11/1989 | Whitely et al. | 435/6 |
| 4,925,785 | 5/1990 | Wang et al. | 435/6 |
| 4,988,617 | 1/1991 | Landegren | 435/6 |
| 5,241,070 | 8/1993 | Law et al. | 546/107 |
| 5,242,794 | 9/1993 | Whiteley | 435/6 |
| 5,312,910 | 5/1994 | Kishore et al. | 536/23.2 |
| 5,407,798 | 4/1995 | Martinelli et al. | 435/6 |

FOREIGN PATENT DOCUMENTS

| | | | |
|---|---|---|---|
| 0336731A2 | 10/1989 | European Pat. Off. | C12Q 1/68 |
| 0473155 | 8/1991 | European Pat. Off. | C12Q 1/68 |
| 8909835 | 10/1989 | WIPO | C12Q 1/68 |
| 9117239 | 11/1991 | WIPO | C12M 1/18 |

OTHER PUBLICATIONS

Barnay, F., 88 Proc Natl. Acad. Sci. USA 189, 1991.
Innis, et al, PCR Protocols, Academic Press, 1990.
Kerem, B., et al, 87 Proc. Natl. Acad. Sci. USA 8447, 1990.
Landegren, et al, 241 Science 1077, 1988.
Landegren, 15 BioEssays 761, 1993.
Plaha, et al, 14 BioTechniques 566, 1993.
Riordan, J.R., et al, 245 Science 1066, 1989.
Saiki, R.K., et al, 230 Science 1350, 1985.
Saiki, R.K., et al, 239 Science 487, 1988.
Wu, D.Y., et al, 4 Genomics 560, 1989.
Zielenski, et al, 10 Genomics 214, 1991.
Klausner, A. et al, Biotechnology, p. 471, Aug., 1983.
Maniatis, T. et al, Molecular Cloning. A Laboratory Manual. Cold Spring Harbor publication, NY., p. 146, 1982.
Meinkoth, J. et al, 138 Analytical Biochemistry 267, 1984.
Nickerson, D. et al, 87 Proc. Natl. Acad. Sci. USA 8923, 1990.
Maniatis in Molecular Cloning a Laboratory Manual, Cold Spring Harbor, 1982, pp. 140–144, 202, 388, 447.
Tchurikiv et al. Febs Lett 297: 233–36 (Abstract Provided), 1992.

*Primary Examiner*—W. Gary Jones
*Assistant Examiner*—Dianne Rees
*Attorney, Agent, or Firm*—Arthur S. Morgenstern; Robert P. Blackburn

[57] ABSTRACT

A new method has been developed for conducting a gene probe assay. The preferred technique involves (1) using a gene amplification technique (e.g., PCR) to multiply the gene sequence of interest and (2) using a hybridization—ligation detection methodology, wherein the sequences of probes hybridized to the target sequence allow for separation and detection (e.g., probes might contain a combination of magnetic particles and acridinium esters) to determine if a specific sequence is present.

47 Claims, 17 Drawing Sheets

DELTA F-508 ALLELE

```
             ATATAAGTAGTATCCTTTGTGGTTACTATAAAAGAAATTACCACGGT
PMP-SPACER-TATATTCATCATAGGAAACACCAATGATATTTTCTTTAATGGTGCCA
                                                        DMAE
                         508.CF-DMAE
```

NORMAL ALLELE

```
             ATATAAGTAGTATCCTTTGTGGTTTCTACTATAAAAGAAATTACCACGGT
PMP-SPACER-TATATTCATCATAGGAAACACCA   ATGATATTTTCTTTAATGGTGCCA
                                                           DMAE
                         508.CF-DMAE
```

DELTA F-508 ALLELE

```
             ATATAAGTAGTATCCTTTGTGGTTACTATAAAAGAAATTACCACGGT
PMP-SPACER-TATATTCATCATAGGAAACACCAATGATATTTTCTTTAATGGTGCCA
                         A─┐
                         A─┤  508.NOR-LEAE            LEAE
                         G─┘
```

NORMAL ALLELE

```
             ATATAAGTAGTATCCTTTGTGGTTTCTACTATAAAAGAAATTACCACGGT
PMP-SPACER-TATATTCATCATAGGAAACACCAAAGATGATATTTTCTTTAATGGTGCCA
                                                             AE
                         508.NOR-LEAE
```

Figure 1

ΔF-508 PROBES

```
  1630         1640          1650         1660        1670
   |            |             |  ΔF-508    |           |
T GGC ACC ATT AAA GAA   AAT ATC ATC TTT GGT GTT TCC TAT GAT GAA TAT AG
       508.NOR-AE                        PMP.508
```

ΔI-507 PROBES

```
  1630         1640          1650         1660        1670
   |            |             | ΔI-507     |           |
T GGC ACC ATT AAA GAA   AAT ATC ATC TTT GGT GTT TCC TAT GAT GAA TAT AG
       507.NOR-AE                        PMP.507
```

Figure 3

HYBRIDIZATION OF ΔF-508 PROBES      HYBRIDIZATION OF ΔI-507 PROBES

NORMAL                              NORMAL
          TGGTTTCTACTATAA                     TGGTTTCTACTATAA
5' PMP  ACCA     ATGATATT  3' AE    5' PMP  ACCAAAG    ATATT    3' AE

ΔF-508                              ΔF-508
          TTGTGGTTACTATAA                     TTGTGGTTACTATAA
5' PMP  AACACCAATGATATT   3' AE     5' PMP  AACACCAAAGATATT    3' AE

ΔI-507                              ΔI-507
          TGGTTTCTATAAAAG                     TGGTTTCTATAAAAG
5' PMP  ACCAATGATATTTTC   3' AE     5' PMP  ACCAAAGATATTTTC    3' AE

Figure 4

5' ATGAGGGAGGTTGTGAGGXYCTGCCCCACCATGA 3'

3' TACTCCCTCCAACACTCCX
                    \
                     P
                       YGACGGGGGTGGTACT 5'
                       \
                        OH

Figure 14

HYBRIDIZATION-LIGATION ASSAYS FOR THE DETECTION OF SPECIFIC NUCLEIC ACID SEQUENCES

This application is a continuation of application Ser. No. 08/222,613 filed Apr. 4, 1994, now abandoned.

BACKGROUND OF THE INVENTION

Gene probe techniques have become an important analytical tool for predicting the incidence of inherited disease and in diagnosing existing medical conditions. However, the currently-used techniques are slow, laborious and involve the use of harmful chemicals. Some procedures used in the gene probe field were discussed recently by Plaha et al (14 BioTechniques 566, 1993). Current gene probe techniques typically involve the use of electrophoresis, frequently on long polyacrylamide gels. Several of the chemicals to which the lab personnel are exposed are considered to be hazardous. Namely, the acrylamide monomer, some of which may remain in the polymeric gel, is considered to be a neurotoxin. The ethidium bromide used as the staining agent is a mutagen. Polyacrylamide gel electrophoresis typically requires several hours, while the analysis using the new gels described in Plaha require 16 hours for a single run. Other techniques use radioactive markers, which require the use of special handling controls and disposal techniques. Also, the other aspects of the current procedures require a relatively long period of time. (For example, the Southern Blot procedure requires about 48 hours to complete.)

Furthermore, the electrophoresis technique itself may produce uncertain results. First, ethidium bromide techniques, are often not very sensitive. Second, the conditions to adequately separate the different gene fragments must be developed. Third, the results are nearly always qualitative, not quantitative. In addition, the inability to distinguish fragments of DNA which are the same or similar size but differ in sequence, even by a single base, also limits the usefulness of past procedures.

Limitations on the sensitivity inherent to DNA based assays may be overcome by the polymerase chain reaction (PCR). The amplification of a specific sequence by PCR enables the detection of that sequence when present in a sample in extremely low amounts (Saiki, et al., 230 Science 1350, 1985). Although the PCR technique can amplify DNA sequences to overcome the sensitivity limitations that existed before PCR was available, a number of problems remain attendant with the use of PCR. The products of a PCR reaction often include artifacts due to primer-dimers and non-specific priming events, especially in the absence of the target sequence in the sample. By virtue of its exquisite sensitivity, PCR is susceptible to false positive results due to contamination. The PCR technique itself does not readily allow the discrimination of small differences between sequences such as point mutations which may underly genetic diseases, such as in cystic fibrosis. As a consequence of these limitations, verification of the presence of the specific target sequence after amplification by PCR is a desirable if not an essential step in a DNA assay.

Earlier workers have used hybridization and ligation techniques as a precursor to analyzing samples on various gels. (See, Landegren et al, 241 Science 1077, 1988). However, these techniques are slow, inconvenient and are not amenable to usage on automated instruments.

A novel analytical method has been developed, which eliminates the drawbacks of the current techniques for the analysis of DNA sequences and provides quicker and more accurate results. The instant novel technique can be utilized along with PCR to improve accuracy in gene probe assays.

SUMMARY OF INVENTION

A new method has been developed for conducting a gene probe assay. The preferred technique involves (1) using a gene amplification technique (e.g., PCR) to multiply the gene sequence of interest and (2) using a hybridization—ligation detection methodology, wherein the sequences of probes hybridized to the target sequence allow for separation and detection (e.g., probes might contain a combination of magnetic particles and acridinium esters) to determine if a specific sequence is present.

BRIEF DESCRIPTION OF THE DRAWINGS

FIG. 1: The probe assay formats used for the detection of the delta F-508 and normal alleles (SEQ ID NOs:5–7).

FIG. 3: A portion of the sequence of exon 10 of the CFTR gene in the vicinity of the sites for the delta F-508 and delta I-507 mutations (SEQ ID NO:7, 8, 10). Sequences underlined are complementary to the sequences of probes immobilized on paramagnetic particles (PMP.508 (SEQ ID NO:5) or PMP.507(SEQ ID NO: 9)and labeled with acridinium ester (508.NOR (SEQ ID NO:7) or 507.NOR).

FIG. 4: The hybrids formed between the probes for the delta F-508 assay and delta I-507 assay and the various alleles (SEQ ID NOs:5,7,9).

FIG. 14: The p53 model for systematic evaluation of ligation specificity. The top sequence is that of the target (region flanking codon 175 of the p53 gene). The probe sequences are on the bottom. The positions marked "X" and "Y" were systematically varied with the four nucleotides.

DETAILED DESCRIPTION OF THE INVENTION

Figure 2:
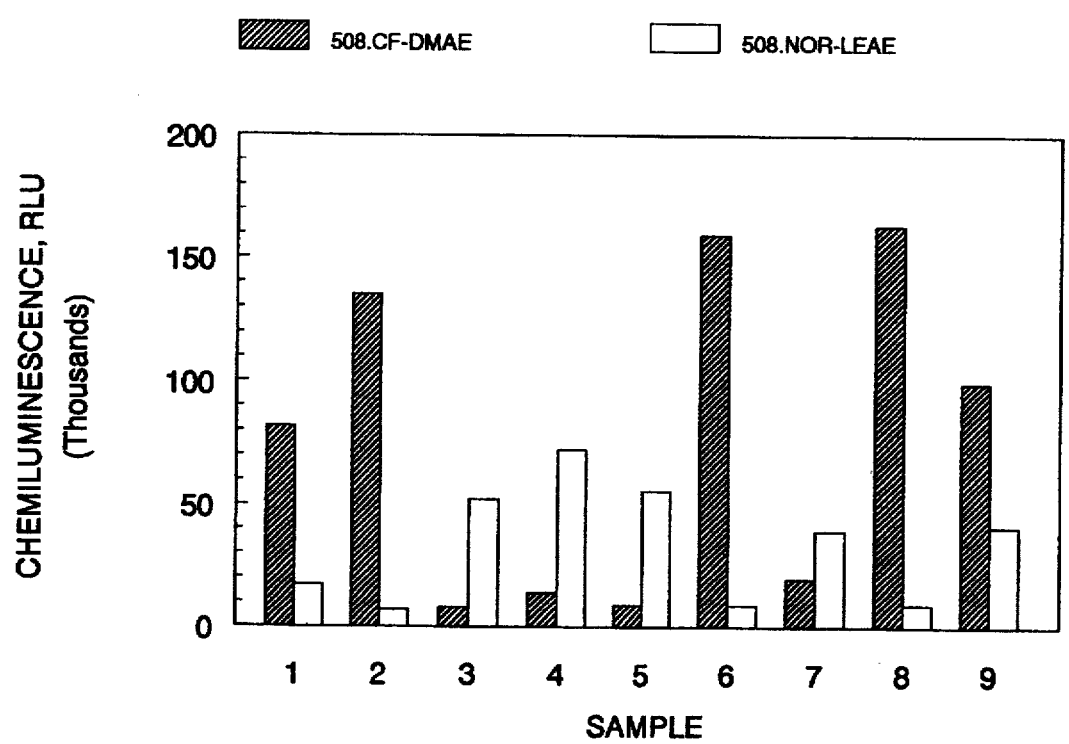
FIG. 2: The results of the HLM for the simultaneous detection of delta F-508 and normal alleles in nine samples of human DNA that have been amplified by PCR. The probe specific for the delta F-508 allele was labeled with DMAE and the probe specific for the normal allele was lableled with LEAE.

The novel technique has been developed for gene probe analyses. This first step of DNA analysis generally involves using an amplification (e.g., PCR) technique to multiply the sequence of interest. Obviously, if sufficient quantity of the unknown sequence is present in the assay sample, amplification may not be needed. Following the amplification process, a hybridization-ligation methodology (HLM) is used to confirm the identity of the amplification product. To help identify the gene sequence, an easily separable particle (for example, a magnetic particle) is used along with an identifiable moiety (for example, a luminescent marker such as an acridinium ester).

The initial part of the technique involves the use of an amplification procedure to multiply the sequence being investigated if insufficient quantity of the sequence to be identified is present. PCR techniques have been known for several years. For example, Saiki et al described an enzymatic amplification technique for β-globulin genomic sequences by providing 2 oligonucleotide primers flanking the region to be amplified, annealing the primers to strands of denatured genomic DNA and extending them with a DNA polymerase from E. coli or Thermus acquaticus and deoxyribonucleosidetriphosphates, and repeating cycles of denaturation, annealing and extension (Saiki et al (230 Science 1350, 1985); Saiki et al (239 Science 487, 1988)). Various amplification techniques have been developed recently (e.g., ligase chain reaction (LCR) and Qβ Replicase), and any of the amplification techniques can be used instead of PCR or in combination with one or more other amplification techniques. Furthermore, it is anticipated that other amplifying techniques will be developed. The exact technique used for amplification is immaterial to the invention herein, and those with knowledge in gene probe procedures are assumed to be familiar with the overall techniques used therein and the reasons for prefering one technique over another. The critical fact is that the relatively small sample of DNA is amplified so that the analytical technique used thereon is more sensitive than it normally would be.

Typically PCR techniques involve the procedure described above. There are many variations of this basic technique known to those with skill in the art, for example those described in PCR Protocols (eds. Innis, M A, Gelfand, D H, Sninsky, J J, and White, T J, Academic Press, 1990). Details of one example of how a PCR reaction is run is described in detail in the examples herein.

Once an amplified sample is available, this material is analyzed by HLM. In HLM, the sequence which is complementary to some or all of the target sequence is incorporated into 2 or more probes which are reacted with the target oligonucleotide. Much of the discussion here relates to the use of only 2 probes, but more than 2 can also be used, as discussed below. One portion of the complementary sequence is attached to an insoluble material that can easily be separated from a reaction mixture. For example, a magnetic particle might be used. Another possible material is a material that can be separated by centrifugation from the reaction mixture. The second portion of the complementary sequence is attached to a material that can be detected by an analytical technique. For example, a chemiluminescent material, such as an acridinium ester, might be used. Other examples are fluorophores or chromophores. These 2 complementary sequences are hybridized to the target sequence. The hybridization solution contains salt, typically approximately 500 to 700 mM NaCl, with concentrations of about 600 mM being most preferred. The hybridization is carried out at elevated temperature (e.g., 45° C.). After hybridization, the insoluble properties of one of the probes is used to separate the hybridized from unhybridized probe with the label. A ligase is then used to attempt to join the 2 complementary sequences of the probes. If the 2 complementary sequences precisely match the target in the immediate region of the junction of the two probes, the terminal nucleic acids are close enough to each other to be connected by the ligase. On the other hand, if the target sequence is sufficiently different from the suspected target, the terminal nucleic acids on the probes are sufficiently far from each other so that they cannot be joined by the ligase. For example, if the target has a deleted nucleotide at the place where the 2 probes meet, the terminal nucleotide on one probe will overlap the other probe, and the two probes will not be ligated. Similarly, if the target has an inserted nucleotide, the 2 probes will not be close enough to each other to permit ligation to occur. Furthermore, if there is a mismatch at the location where the 2 probes meet, the 2 probes will not be ligated efficiently under conditions defined herein.

Although the ligation proceeds as described above, depending on whether the terminal bases of the probes couple or fail to couple with the target, those with skill in the art will recognize that the mismatching of bases on the probe away from the terminal positions may also have some effect on the binding of the probe to the target. For example, if a base located on the probe several base positions away from the terminal base fails to bind with the corresponding base on the target, there may not be sufficient discordance between the probe and target to prevent the terminal probe bases from being ligated. Steric factor and the totality of binding between the probe and target will have an effect on whether the instant technique is totally effective in determining the composition of the target. On the other hand, it should be noted that discordance away from the junction of the probes may have a sufficient effect so that the two probes will not be ligated. An example below shows a case in which discordance at a site 2 bases away from the junction of the probes causes sufficient interference that the probes were not ligated.

Similarly, by using sets of probes that are expected to hybridize and ligate to a portion of the normal sequence, it is possible to determine whether the target contains a mutation. If it is found that hybridization or ligation do not occur, it can be concluded that the mutation probably occurs in that portion of the target being examined. By moving to the next portion of the target, a similar experiment can be run. Thus, by moving sequentially along the target, one can determine the site or sites on the target where mutations are found and then proceed to design experiments to identify the exact mutation which occurs at each of the mutation sites.

The ligation is carried out under conditions which will ensure the specificity of the reaction (see examples below). Ligation can be carried out using one of the many ligating reagents available, such ligating reagents typically achieving ligation by chemical or enzymatic action. One important difference between the conditions utilized here vs. the prior art is that a much higher salt concentration has been found to assure ligation specificity. The previously used salt concentration (200 mM NaCl) had been found to permit ligation of mismatched probes. In the instant invention, it has been found that higher salt concentrations yield unexpectedly improved specificity. For example, to attain the most specific ligation with T4 DNA ligase, the salt concentration is typically approximately 500 to 700 mM NaCl, with concentrations of about 600 mM being most preferred and concentrations up to about 1000 mM being usable.

Variations in the ligation process are possible. For example, many different ligating agents can be used, and examples showing the use of T4 DNA-ligase and Taq DNA-ligase are shown herein. Furthermore, it may be preferred to include in the Taq ligase buffer other components which may increase the sensitivity of the reaction. For example, it has been found that the inclusion of tRNA reduces background signal which is caused by non-specific bonding of the labeled probe After the ligation step is undertaken, a denaturation step separates the target sequence from that of the probes and ligated from unligated probe. The material connected to the insoluble material can then be separated from the reaction mixture by centrifugation, application of a magnetic field or other appropriate procedure, and the presence of any label connected to the insoluble material due to the action of the ligase can be determined.

By using the disclosed components, the separation of the target material can be achieved using a technique other than chromatography or electrophoresis. Thus the technique can be accomplished much faster than if electrophoresis or chromatography were used. Furthermore, the detection technique can be a more quantitative one, such as the measurement of radioactivity, fluorescence or luminescence. Other detection methods can utilize commonly available techniques that permit the subsequent addition of the label. For example, the probe might have chemically attached thereto biotin, and, after separation of the probes, the label, being bonded to avidin or streptavidin, can be reacted thereto, thus forming a probe linked to a detectable label. Thirdly, the technique can now be utilized in some of the automated instruments, such as the ACS 180 instrument manufactured by Ciba Corning Diagnostics Corp. of Medfield, Mass.

It should be noted that a variation of the instant technique can be used to determine information about the sequence on the target. If, after denaturation, it is found that no label is connected to the insoluble probe, a different aliquot of the reaction mixture which has not been denatured can be further analyzed. In that sample, the insoluble marker can be separated (e.g., by the application of a magnetic field, by use of centrifugation, etc.), and the target can be analyzed to determine if the marker probe is attached to the target. If this is found to be the case, the sequence of much of the target polynucleotide can be predicted due to the hybridization of the 2 probes to the target, and further experiments to confirm the sequence in that region of the target (e.g., near the ligation point) can be planned.

Alternatively, a similar analysis can be conducted by denaturing the sample after ligation and then separating the solid phase. In this technique, both the separated solid phase and the supernatant are analyzed for the presence of the labeled probe. If most of the label is found only in the supernatant, it can be concluded that ligation of the probes did not occur, which is an indication of a mismatch at the expected ligation point. However, since the labeled probe became attached to the target, it can be concluded that the target had the expected sequence, or a sequence close to expected, or else the labeled probe would not have hybridized to the target. Thus, even though ligation has not occurred, much can be inferred about the sequence of the target. Furthermore, the sum of the amounts of the label in the supernatant and on the solid phase should approximate the total amount of target in the assay sample. The percentage of the labeled probe which is ligated should indicate the homozygosity or heterozygosity of the sample. In addition the ratio of label on the solid phase to the label in solution can indicate more information about the sequence on the probe, for example the existence of diseases wherein portions of genetic material are replicated (e.g., fragile X). It should be noted that, in conducting these assays, the data have not been found to be exactly the theoretically expected values (i.e., not 100% of the label is found in the solid phase for a homozygous sample). (See example below.)

Thus, by knowing the potential mutations that can occur at a particular site, it is possible to generate a specific probe so that the sequence on the target can be confirmed. If several potential mutations can occur at one site, it is also possible to design several probes, each with a different label, to determine whether it is the normal sequence, and, if it is a mutated sequence, which of the mutations occurs. Similarly, mutations that occur near each other in a target sequence can be determined. In addition, the technique of using two or more differently labeled probes can be utilized in the case where multiple forms of the target are expected, such as in the fragile X case discussed above.

The two different labels used in the same assay may be, for example, a fluorescent donor and fluorescent acceptor pair. In this case, by varying the incident light, the two labels can be used to distinguish among three possible outcomes. If the incident light to the first probe gives fluorescence typical of the first label, this is an indication that only the first target is present. If the fluorescent output is that from the second label, two alternatives are present. If incident light which excites the first label gives fluorescense from the second label, this is an indication that both targets are present. On the other hand, if only the incident light which excites the second label gives fluorescense from the second label, this is an indication that only target two is present.

For example, multiple mutations in one vicinity have been found in variations of cystic fibrosis. For example, the delta F-508 and delta I-507 mutations are both 3 base pair deletions, the positions of these mutations are partially overlapping in the sequence of the CFTR gene. (See Zielenski et al (10 Genomics 214, 1991) for sequence of the CFTR gene.) Analysis of the PCR amplification product spanning this sequence by polyacrylamide gel electrophoresis would not be able to readily resolve these two mutations since the products would have the same size. However, these mutations would be distinguished by the HLM. In addition, exon 11 of the CFTR gene contains the sites of many CF mutations including the G542X mutation at base 1756 (see SEQ ID NO 11) and G551D mutation at base 1784 (see SEQ ID NO 16). After a single PCR amplification of the sequence spanning the sites of these mutations, the presence or absence of both mutations can readily be determined by HLM.

It will be noticed that, although there are some similarities between the HLM technique and ligase chain reaction (LCR), the techniques are, in actuality, very different. LCR itself is an amplification technique that has been known for some time. See, for example, Wu and Wallace, 4 Genomics 560, 1989; also Barany, 88 Proc. Natl. Acad. Sci. USA 189, 1991. In LCR, two portions of oligonucleotides that are each complementary to each chain of a piece of the target gene being amplified (with the two together corresponding to the entire target gene portion) are added to the gene sample to be amplified along with a ligase. If the added oligonucleotides complement the target sequence, the ligase will join the two oligonucleotides. LCR is an amplification technique wherein, knowing the sequence to be amplified, it is possible to add to the reaction mixture fragments that are complementary to the target so that, when ligase is added, ligation occurs and the target is amplified. LCR is intended to be repeated for several cycles so that large quantities of the desired sequence can be produced.

HLM, on the other hand, is an analytical technique, wherein probes to one or more suspected sequences which are likely to be found in the target are added to the target. The probes are joined either to a material which can aid separation from the reaction mixture or to a label. Furthermore, the reaction is intended to be run for only one cycle.

There are many variations possible in the HLM procedures. For example, one may combine the detection procedure with column chromatography. One of the oligonucleotide probes in this procedure contains a substituent that will cause it to adhere to a column chromatograph. For example, one of the probes is biotinylated, and the ligated products are separated on avidin-sepharose. The other oligonucleotide might contain a fluorescent marker. Thus, when the sample is passed through a column chromatograph, those oligonucleotides that have been ligated will adhere to the chromatograph and be fluorescent. Thus fluorescence within the column is an indicator that the ligation has occurred. The use of the fluorescence donor/acceptor pair discussed above can also be used in the column chromatography technique.

Another variation deals with the moieties to which the probes are connected. Although in most cases one probe will be connected to a moiety that permits separation of the ligated probes and the second probe will be attached to a label moiety, it is possible that the two probes can be attached to other moieties, such as other sequences. For example, the probes can be connected to the two components of the midivariant sequence, if the QB replicase system is being used. In this case, one probe is connected to one portion of the midivariant sequence (e.g., midivariant A) and the second is connected to the second portion of midivariant sequence (i.e., midivariant B). If replication is observed in the reaction with QB replicase after the ligation step, it is an indication that the two probes were ligated. The fact that the probes were ligated is an indication that the probes have the same sequence as the target.

A further variation of the technique involves the timing for the addition of the flash reagent when using certain luminescent labels, such as acridinium esters. After denaturation and separation of the ligated probes, it is possible to add DNAase before the addition of the flash reagent. This will allow for a more sensitive test, since it has been found that the presence of the insoluble probe interferes at times with the amount of light given off when the flash reagents are added. The separation of the insoluble probe before the addition of the flash reagent thus allows a higher specific signal to be generated.

Another variation concerns the number of probes which are utilized. Although the preferred technique involves the use of two probes, one which aids in separation and one which aids in detection, it should be noted that more that two probes can be used. In this case, one of the probes contains the separating moiety and one the detection moiety. If the separating moiety is on one terminal probe and the label moiety on the other terminal probe, the probes between then would not need to contain a label. In this experiment, if, after ligation, the label probe is attached to the separating probe, it can be concluded that the intermediate probes also hybridized to the target, for, if this were not the case, the label probe would not be ligated to the probe moiety which includes the separating probe. Another variation of the multiple probe experiment is the one where one probe containd the separating moiety and all the other probes are labeled. In this case, after ligation, the amount of label attached to the separated moiety is an indication of whether all the probes were ligated. The use of more than 2 probes, when combined with the variations discussed above (e.g., analysis with and without ligation, analysis before denaturation, etc.) leads to a number of analytical variations which will be apparent to those with ordinary skill in this area.

Furthermore, the location of the separating or detecting moiety can be varied. Although it is preferred that they be at the terminal end of a probe, it is possible that they be connected to the probe in any location so long as they do not interfere with hybridization and ligation.

A further advantage of the novel technique is that it is now possible to descriminate between two mutations that are closely related to each other (e.g., mutations that occur at adjacent nucleotides).

A further advantage of the instant invention is that different markers can be used on different probes in the same experiment. Thus, for example, the presence of one of two possible mutations can be determined in one test, with each probe using a different marker. Both markers could be separated from the sample and the two could be distinguished by their differing absorption spectra, for example. Furthermore, by using different insoluble particles, the 2 probes can be separated from each other before analysis. For example, if one probe relies on an insoluble non-magnetic particle and the other uses an insoluble magnetic particle, the magnetic field could be applied first in order to remove the magnetic particles and the markers attached thereto, and the remaining solution can be centrifuged to remove the non-magnetic insoluble particles with its attached marker. Other variations of these separation techniques will be apparent to those with skill in the art. Thus, these two markers could still be distinguished from each other even though they both have the same label. By combining in one experiment variations of techniques utilizable for both separation and detection, it is possible to determine the presence of one of several mutations or other genetic variations in the one experiment. For example, magnetic (M) particles could be used on some probes, non-magnetic (NM) on others; some of the second oligonucleotides in the probe could use chemiluminescent material A, while others could use chemiluminescent material B. Thus, by varying just these 2 parameters, 4 mutations could be detected in one experiment. (I.e., where the adducts to the probes are M-A, NM-A, M-B, NM-B) By utilizing particles that can be separated from each other with different markers (i.e., those with different spectral or other characteristics), it would be possible to detect many genetic variations in one experiment.

A further advantage of the novel procedure is that the technique is more sensitive than previous techniques. This increased sensitivity is due to several factors. For example, the analytical techniques for determining the presence of target material are more sensitive; the solution technique of separating the insoluble particle and analyzing the marker attached thereto is much more sensitive than the process of using electrophoresis to separate the components and to rely on staining to qualitatively and quantitatively determine the presence of the target.

Further variations of the above procedure are possible. For example, after the insoluble particles are separated from the reaction mixture, the quantity of target present can be determined by measuring the amount of marker while the marker is still attached to the insoluble material when the insoluble particles are precipitated (as, for example, using a classical quantitative analysis on insoluble material). Alternatively, after the insoluble particles are separated from the reaction mixture, the particles can be resuspended and the marker determined while on the resuspended particle. Furthermore, the marker can be separated from the insoluble particle and be measured when both the marker and insoluble particle are in solution or suspended. Also, after separation of the marker from the insoluble particle, the insoluble particle can be separated from the solution and the marker can be measured in the absence of the insoluble particle.

The target sequence amplified in the PCR reaction with these primers consisted of 97 bp (94 bp for delta F-508 allele) spanning bases 1611–1708 of the CFTR gene (3).

The PCR reactions (75 ul) contained 30 pmol each primer, 1.9 mM $MgCl_2$, 200 uM each ATP, TTP, GTP, and CTP; and 2.5 U Taq DNA polymerase. After denaturation at 95° C. for 5 min, the samples were amplified by 30 cycles of PCR consisting of annealing at 60° C. for 45 sec, extension at 72° C. for 1 min and denaturation at 95° C. for 45 sec. After the last cycle the samples were incubated at 72° C. for 5 min.

An aliquot of the PCR reaction solution was denatured and then added to the chemiluminescent detection reaction: 100 ul TE, 4X SSC, 0.1% BSA, 0.02% Tween-20, 5% dextran sulfate containing 10 ug paramagnetic particles (PMP) with the immobilized probe (PMP) and 100 fmol of each acridinium ester (508.CF-DMAE and 508.NOR-LEAE) labeled probe. The sequences of the detection probes were:

PMP.508 (SEQ ID NO 5): 5' CCT AGT CCA AGT ACG GCG CCG AAG AGG CCC TAT ATT CAT CAT AGG AAA CAC CA 3'
508.CF (SEQ ID NO 6): 5' ATG ATA TTT TCT TTA ATG GTG CCA 3'
508.NOR (SEQ ID NO 7): 5' AAG ATG ATA TTT TCT TTA ATG GTG CCA 3'

In addition to detecting specific DNA sequences, HLM may also be used to detect specific RNA sequences provided that the ligase used can ligate probes which are hybridized to an RNA target. The technique can also be used to analyze viral materials and other sequences of polynucleic acids. In addition, since the examples illustrate the ability of HLM to distinguish sequences which differ at positions at sites other than the ligation junction of the probes, this method can be readily adapted to scan large segments of sequence even up to whole genes for alterations distinct from a normal sequence.

Further variations of the invention will be apparent to those with ordinary skill in the art. The following examples illustrate various aspects of the invention but are not intended to limit its usefulness.

EXAMPLE 1
Simultaneous Detection of Normal and Delta F-508 Alleles Using Chemiluminescent Hybridization Ligation Assay with DMAE and LEAE Labeled Probes A chemiluminescent hybridization-ligation method was tested for its ability to detect the delta F-508 (SEQ ID NO 1) mutation in cystic fibrosis in samples of human DNA amplified by PCR. In addition, the presence of both the normal (SEQ ID NO 2) and delta F-508 alleles was simultaneously determined for each sample by using probes specific for each allele but labeled with two different acrindinium ester derivatives (DMAE and LEAE). The DMAE derivative (dimethyl acridinium ester) chemiluminesces at the shorter wavelength range (400–500 nm) and LEAE (longer wavelength emitting acridinium ester) chemiluminesces at the longer wavelength range (500–600 nm)

Nine samples of human DNA (250 ng) obtained from an outside laboratory were amplified by the polymerase chain reaction (see Saiki et al, 239 Science 487, 1988). The primers used were obtained from Genset (Paris, France) and had the following sequences:
C16B (Sequence ID NO 3):5' GTT TTC CTG GAT TAT GCC TGG CAC 3'
C16D (Sequence ID NO 4):5' GTT GGC ATG CTT TGA TGA CGC TTC 3'

The possible assay formats are summarized as shown in FIG. 1.

The probes were hybridized to the PCR product at 45° C. for 15 minutes. Unhybridized AE probes were removed by magnetic separation of the particles and decanting the supernatant. The particles were washed with 2X SSC/0.1% Tween-20.

Hybridized probes were ligated by resuspending particles in 100 ul 50 mM Tris, pH 7.6, 10 mM $MgCl_2$, 1 mM ATP, 1 mM DTT, 5% polyethelyene glycol 8000 and 200 mM NaCl containing 2 U T4 DNA ligase. Reactions were incubated at 37° C. for 15 minutes. After separating and washing the particles as described, the hybridized but non-ligated AE probes were dissociated by resuspending the particles in 150 ul $H_2O$ and incubating at 65° C. for 10 minutes. The particles were separated and the supernatant containing dissociated AE probe removed. The particles were washed once as described and then resuspended in 100 ul 10 mM Tris, pH 7.5, 10 mM $MgCl_{12}$, 1 mM EDTA, and 0.05 ug/ul DNase I (BRL). The particle suspension was flashed using standard flash reagents (see, for example, Law et al, U.S. Pat. No. 5,241,070) and the chemiluminescence detected in a dual wavelength luminometer so that the chemiluminescent signals from the two different labels were measured simultaneously.

The results of the chemiluminescent hybridization-ligation assay for PCR amplified product are shown in FIG. 2. The chemiluminescent signal obtained clearly identified the presence of the delta F-508 and normal alleles in the PCR amplified products. As expected, the allele specific probes hybridized to each sample irrespective of genotype (data not shown), the subsequent ligation step discriminated between the sequences of the two different alleles since efficient ligation was observed only at the junction of the hybridized probes which were perfectly complementary with the target sequence (see FIG. 1).

The chemiluminescent detection of these alleles allowed the diagnosis of these samples which was in complete accord with the analysis of the same samples by an independent laboratory with one exception (See Example 2).

Each sample was analyzed with both delta F-508 and normal allele specific AE probes in order to unambiguously assign the genotype of the samples. The magnitude of the chemiluminescence (FIG. 2) also indicated the genotype of the sample in that an intermediate level of chemiluminescence was observed for heterozygous individuals (for example the normal allele in samples 1,7, and 9) relative to the chemiluminescence of the homozygous cases. Sample 7 was an exceptional sample in that the magnitude of the chemiluminescence from the 508.NOR-LEAE probe indicated that the sample was heterozygote for this allele, but the signal from the 508.CF-DMAE probe indicated that this sample was negative for the delta F-508 mutation. Taken together these results suggested that the second allele in this sample contained neither the delta F-508 nor the normal sequence but a second cystic fibrosis mutation instead. These PCR products were also analyzed by electrophoresis on an 8 M urea/10% polyacrylamide gel and the resolved bands visualized by ethidium bromide staining (data not shown). The products from the normal (97 bp) and CF (94 bp) alleles were clearly resolved on the gel, enabling a diagnosis. In addition, heterozygote samples also contained bands resulting from heteroduplex formation which migrated as apparently larger products. In this regard, on the basis of the electrophoretic analysis, samples 1, 7, and 9 appeared identical and would be assigned as delta F-508/ normal heterozygotes. As noted above, on the basis of the chemiluminescent data, although sample 7 was heterozygous for the normal allele, it did not appear to contain the delta F-508 allele. This discrepancy was resolved in Example 2 and illustrated the ability of HLM to provide a more accurate diagnosis compared with standard analytical procedures such as electrophoresis.

EXAMPLE 2
Discrimination of Delta F-508 and Delta I-507 Mutations by Chemiluminescent Hybridization Ligation The delta F-508 mutation is the most common mutation in cystic fibrosis (CF), occurring in approximately 68% of the cystic fibrosis chrmomosomes (3). This mutation is a deletion of three base pairs in exon 10 of the CFTR gene (3). The sequence of exon 10 surrounding this mutation site is shown in FIG. 3. The delta I-507 (SEQ ID NO 8) mutation is a much rarer CF mutation which is also a three base pair deletion that partially overlaps the delta F-508 mutation (FIG. 3). The sequences of these two CF alleles differ by a single base.

The ability of the chemiluminescent hybridization ligation assay to distinguish the delta F-508 and normal alleles was demonstrated in Example 1 . The ability of the assay to distinguish the delta F-508 and delta I-507 alleles was shown in this example. This application requires that the ligation step distinguish sequences which differ at a single position. In addition, the site of the mismatch in these hybrids occurs at one base removed from the ligation junction. The hybrids formed between the delta F-508 and delta I-507 probe sets and the different target sequences are shown in FIG. 4.

The same nine clinical samples of human DNA which had been amplified by the polymerase chain reaction (example 1) were analyzed for the presence of the delta I-507 allele. In this assay, a similar format was followed as in example 1 with the exception that the solid phase and acridinium ester (DMAE) labeled probes were as follows:

| | |
|---|---|
| PMP.507 (SEQ ID NO 9): | 5' CCT AGT CCA AGT ACG GCG CCG AAG AGG CCC TAT ATT CAT CAT AGG AAA CAC CAA AG 3' |
| 507.CF (SEQ ID NO 10): | 5' ATA TTT TCT TTA ATG GTG CCA GGC 3' |

An additional three samples (30, 31, and 32) of PCR amplified human DNA were assayed for the delta F-508, delta I-507, and normal alleles using the same protocol as well as a protocol utilizing Taq DNA ligase (Epicentre Technologies). The thermostablility of Taq DNA ligase permitted the ligation reaction to be carried out at higher temperature as well as allowing the hybridization and ligation steps to be carried. out simultaneously. The buffer for the simultaneous hybridization-ligation consisted of 20 mM Tris, pH 8.3, 200 mM KCl, 10 uM tRNA, 10 mM MgCl$_2$, 0.5 mM AND, and 0.01% Triton X-100. The reactions contained 100 units Taq DNA ligase. The simultaneous hybridization-ligations were carried out at 60° C. for 30 minutes. The remainder of the protocol was identical to that for the assays employing T4 DNA ligase.

Figure 5:
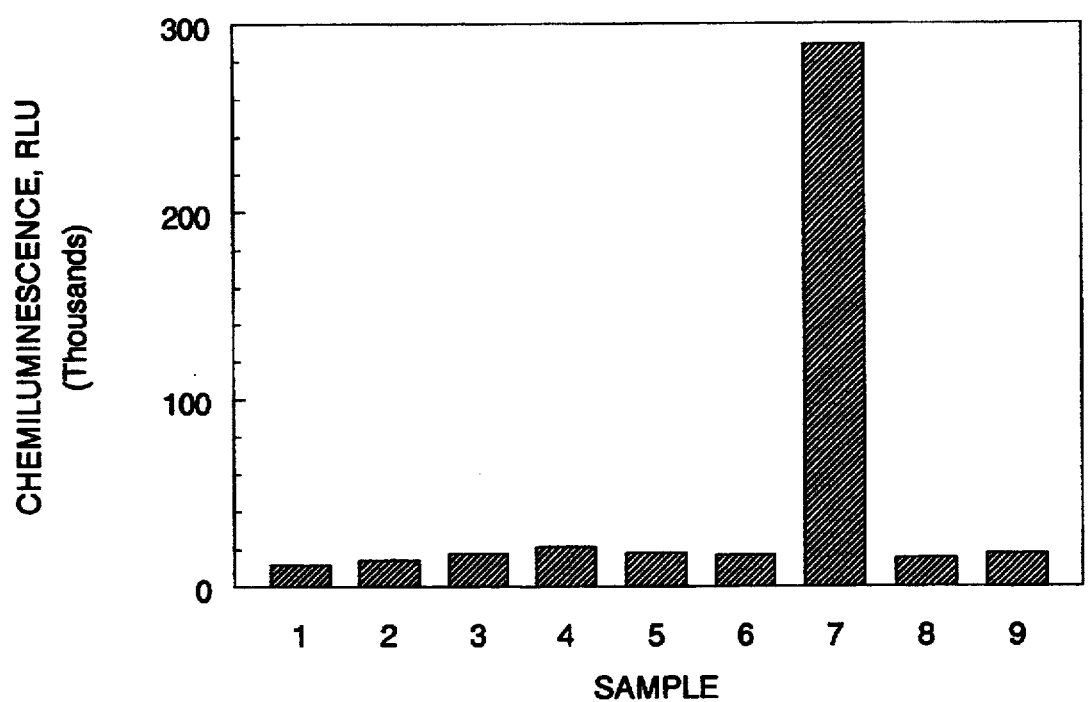
FIG. 5: HLM results for the detection of the delta I-507 mutation in nine samples of human DNA that have been amplified by PCR.

The results of the chemiluminescent hybridization ligation assay of the nine samples are shown in FIG. 5. Only sample 7 was positive for the delta I-507 allele. These results taken together with those of Example 1 permit the following assignments for these samples:

TABLE I

| GENOTYPE OF CLINICAL SAMPLES | | | | | | | | |
|---|---|---|---|---|---|---|---|---|
| 1 | 2 | 3 | 4 | 5 | 6 | 7 | 8 | 9 |
| 508/N | 508/508 | N/N | N/N | N/N | 508/508 | 507/N | 508/508 | 508/N |

Figure 6:
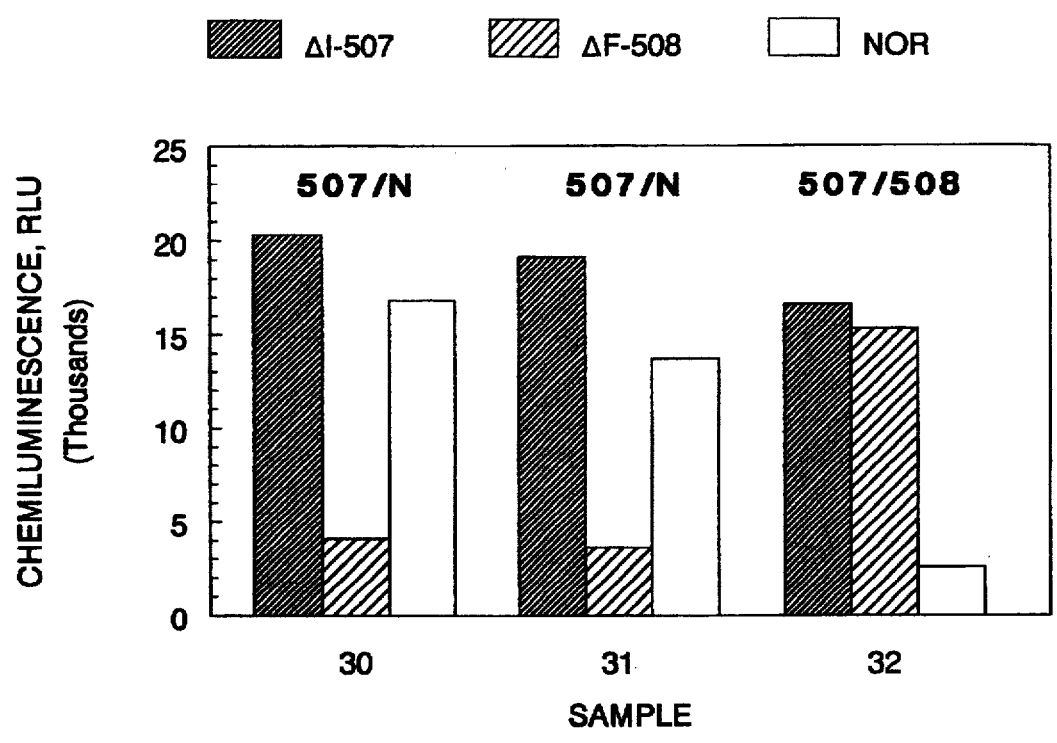
FIG. 6: HLM analysis of three samples of human DNA amplified by PCR for the presence of the normal, delta F-508, and delta I-507 alleles.
Figure 7:
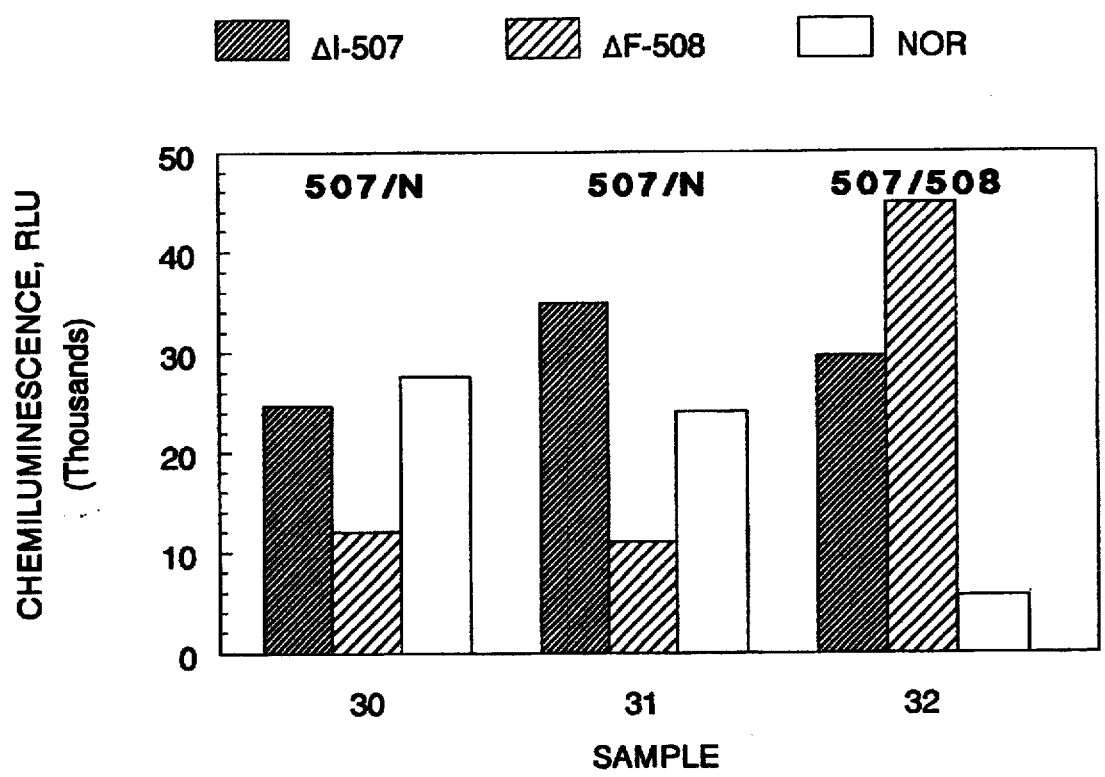
FIG. 7: HLM analysis of three samples of human DNA amplified by PCR using the simultaneous hybridization-ligation protocol with Taq DNA ligase for the presence of the normal, delta F-508, and delta I-507 alleles.

The results of the three additional samples assayed for the delta F-508, delta I-507, and normal alleles are shown in FIGS. 6 and 7. The assignments made for these samples were confirmed by sequencing.

The results shown in examples 1 and 2 illustrate the ability of chemiluminescent hybridization-ligation assay to discriminate sequences differing by a single base even when the site of this difference occurs one base removed from the site of the ligation junction. In this particular application, the cystic fibrosis mutations delta F-508 and delta I-507 were distinguished. This enabled samples that had been previously characterized as delta F-508/N to be correctly assigned as delta I-507/N. The assignment of samples 7 and 30 as delta F-508/N heterozygotes had been made on the basis of the electrophoretic mobility of the PCR products of these samples. But analysis of these PCR products by polyacrylamide gel electrophoresis fails to readily distinguish the delta F-508 and delta I-507 mutations, since both mutations consist of three base pair deletions, the PCR products from these alleles are the same size.

EXAMPLE 3
Assay for the G542X Cystic Fibrosis Mutation

The previous examples have demonstrated the ability of the chemiluminescent hybridization-ligation assay to distinguish the normal and cystic fibrosis alleles at the sites of the delta F-508 and delta I-507 mutations. A third cystic fibrosis mutation, G542X (SEQ ID NO 11), is a point mutation occurring in exon 11 of the CFTR gene. The current method for detecting this mutation requires sequencing, which is a lengthy and laborious procedure. The chemiluminescent hybridization-ligation assay to detect this mutation must be able to distinguish the single base substitution which differs between the normal (SEQ ID NO 12) and cystic fibrosis alleles.

The same simultaneous hybridization-ligation assay using Taq DNA ligase as described in Example 2 was used in the G542X assay. The sequences of the G542X probes were:

| | |
|---|---|
| PMP.G542X (SEQ ID NO 13): | 5' CCT AGT CCA AGT ACG GCG CCG AAG AGG CCA CTC AGT GTG ATT CCA CCT TCT C 3' |
| G542X.CF (SEQ ID NO 14): | 5' AAA GAA CTA TAT TGT CTT TCT CTG CAA 3' |
| G542X.NOR (SEQ ID NO 15): | 5' CAA GAA CTA TAT TGT CTT TCT CTG CAA 3' |

Figure 8:
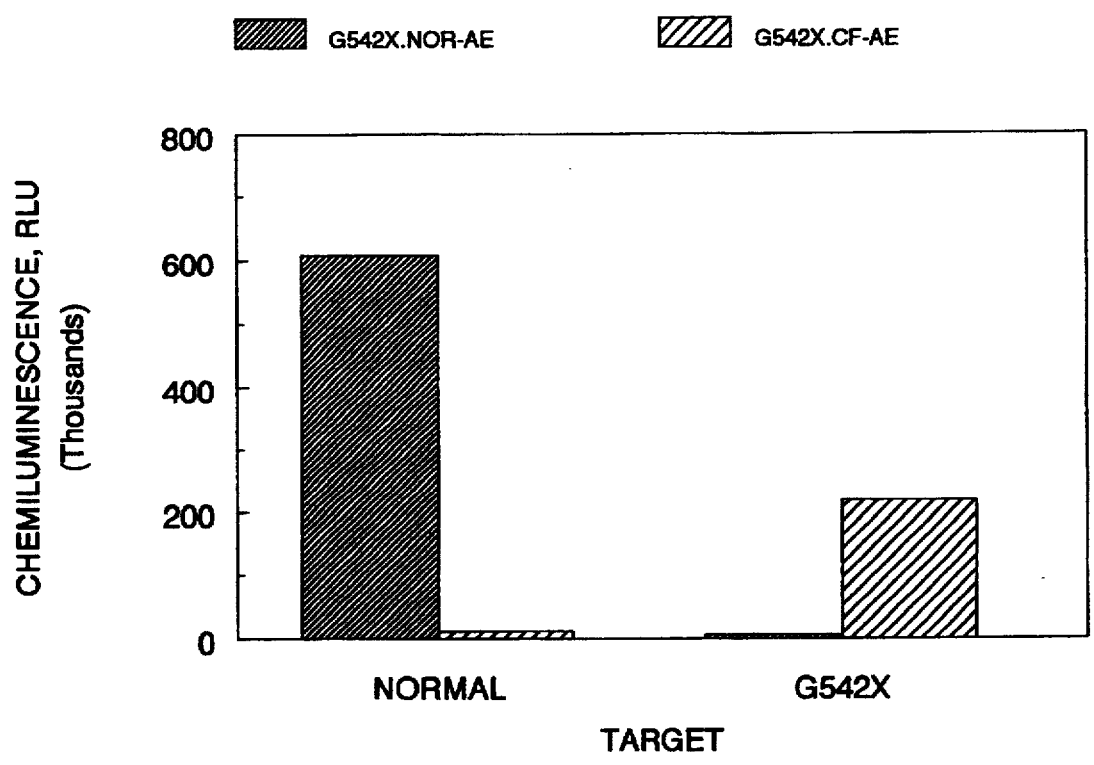
FIG. 8: HLM discrimination of the G542X and Normal alleles.

The results of the assay are shown in FIG. 8 and indicate that the only G542X.CF probe was ligated with the G542X sequence and only the G542X.NOR probe was ligated with the normal sequence. In this example, T-C and G-A mismatches at the ligation junction were not efficiently ligated.

EXAMPLE 4
Simultaneous Assay for Delta F-508 and G542X

The chemiluminescent hybridization-ligation assay can be used for the simultaneous detection of multiple sequences. One illustration of this capability was the simultaneous detection of the delta F-508 and normal alleles in a single assay (Example 1). Another application is the detection of two or more mutations which underly an inherited disease or cancer. For example, more than 200 mutations have been described which underly cystic fibrosis. The delta F-508 mutation is the most common one, occurring in approximately 68% of the cystic fibrosis chromosomes. The second most frequent cystic fibrosis mutation is the G542X mutation, a point mutation occurring in exon 11 of the CFTR gene. Instead of using the two different acridinium ester labels to simultaneously detect the normal and CF alleles at a single locus, the delta F-508 and G542X mutations may be detectd in a single assay. In principle, as many mutations as there are acridinium ester derivatives with distinct chemiluminescent properties, may be detected in a single assay. Alternative labels, such as fluorophores, may permit a still greater number of loci to be simultaneously detected.

Figure 9:
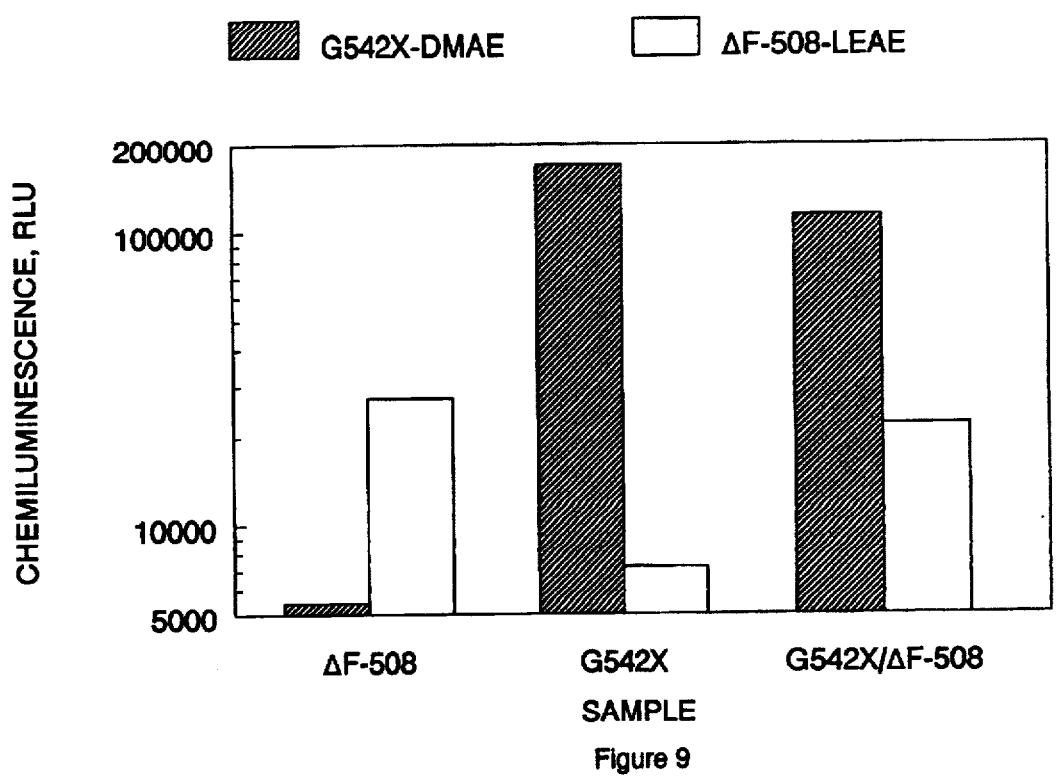
FIG. 9: Simultaneous detection of delta F-508 and G542X mutations by HLM.

A model assay to test feasibility was performed with synthetic target sequences. The assay protocol was the same as that described in Example 2 using Taq DNA ligase and simultaneous hybridization-ligation. Two solid phases and two acridinium ester labeled probes, one set each for the delta F-508 and G542X mutations were used. The probes for the the delta F-508 mutation were the same as those described in Example 1 with the exception that the acridinium ester label was LEAE. The sequences of the G542X probes were the same as those used in example 3. The results of the assay are summarized in FIG. 9 and show that the delta F-508 and G542X sequences were detected with whatever combinations of targets were employed. This demonstrates the feasibility of detecting multiple genetic mutations in the same assay.

EXAMPLE 5
Discrimination of G551D, G551S, and Q552X Cystic Fibrosis Mutations.

Exon 11 of the CFTR gene contains the sites for many other cystic fibrosis mutations in addition to the G542X mutation described in the examples above. The presence of multiple mutation sites in the relatively short span of sequence of exon 11 has heretofore resulted in the necessity of sequencing the PCR product from this exon in order to detect and discriminate these possible mutations. The ability of HLM to simplify analysis of exon 11 cystic fibrosis mutations required that the specificity of this method enable discrimination of closely clustered mutation sites. The G551D mutation (SEQ ID NO 16) is one of the more common cystic fibrosis mutations, accounting for approximately 0.5% of the observed frequency, this is a point mutation in which G1784 in the normal gene (SEQ ID NO 17) is changed into an A. Close to the site of the G551D are the G551S(SEQ ID NO 18) at base 1783, and Q552X (SEQ ID NO 19) at base 178 . In addition the nature of the G551D mutation requires the discrimination of a G-T mismatch by HLM, one of the most difficult mismatches to discriminate (see below). The ability of HLM to detect the G551D mutation and discriminate between it and the other mutation sites near to it was demonstrated in this example.

The sequences of the probes used in the G551D assay were as follows:

| | |
|---|---|
| PMP.G551D (SEQ ID NO 20): | CCT AGT CCA AGT ACG GCG CCG AAG AGG CCC TAA AGA AAT TCT TGC TCG TTG A |
| G551D.CF (SEQ ID NO 21): | TC TCC ACT CAG TGT GAT TCC AC |
| G551D.NOR (SEQ ID NO 22): | CC TCC ACT CAG TGT GAT TCC AC |

In these assays, G551D.CF and G551D.NOR were labeled with $^{32}P$ at their 5' termini. Detection of ligation product was accomplished by liquid scintillation counting. Assays were performed using either the standard T4 DNA ligase and Taq DNA ligase protocols described above as well as modifications to these protocols by altering the salt conditions in order to improve specificity of HLM. For T4 DNA ligase, this involved increasing the NaCl concentration from 200 to 600 mM. The Taq DNA ligase protocol was altered by substituting NaCl for KCl. The exact ligation conditions are indicated with the figures below.

Figure 10:
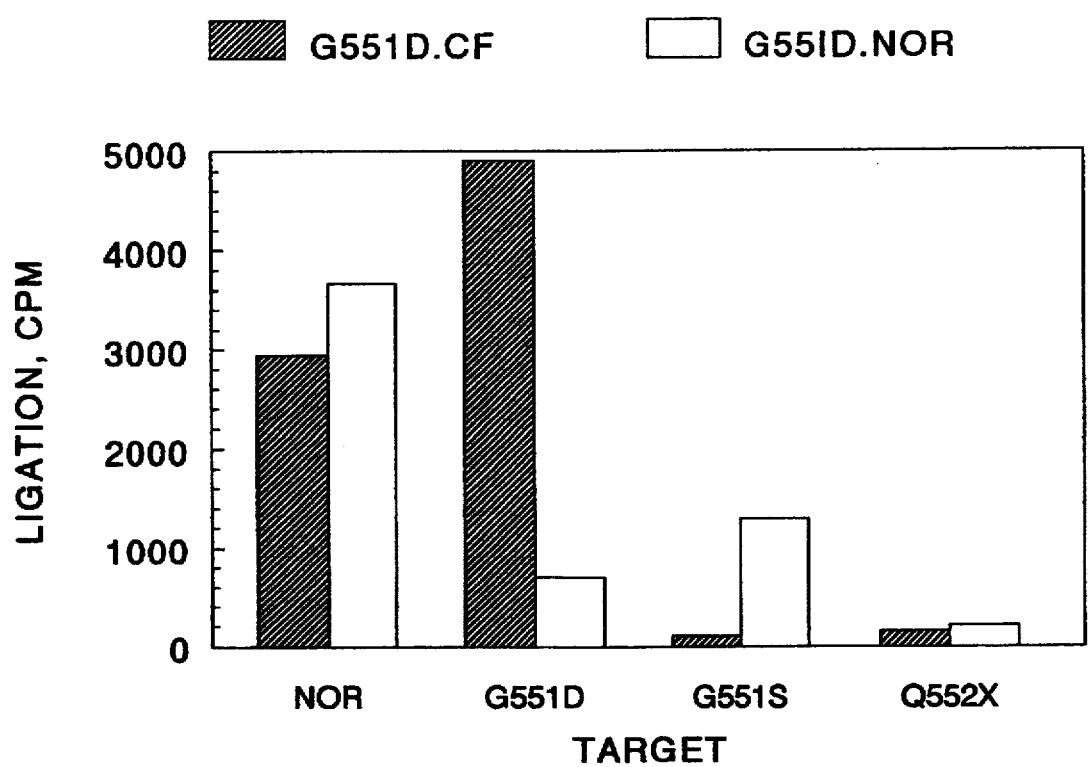
FIG. 10: Discrimination of normal, G551D, G551S, and Q552:K sequences by HLM with $^{32}$P-G551D.NOR or $^{32}$P-G551D.CF using T4 DNA ligase with 200 mM NaCl.
Figure 11:
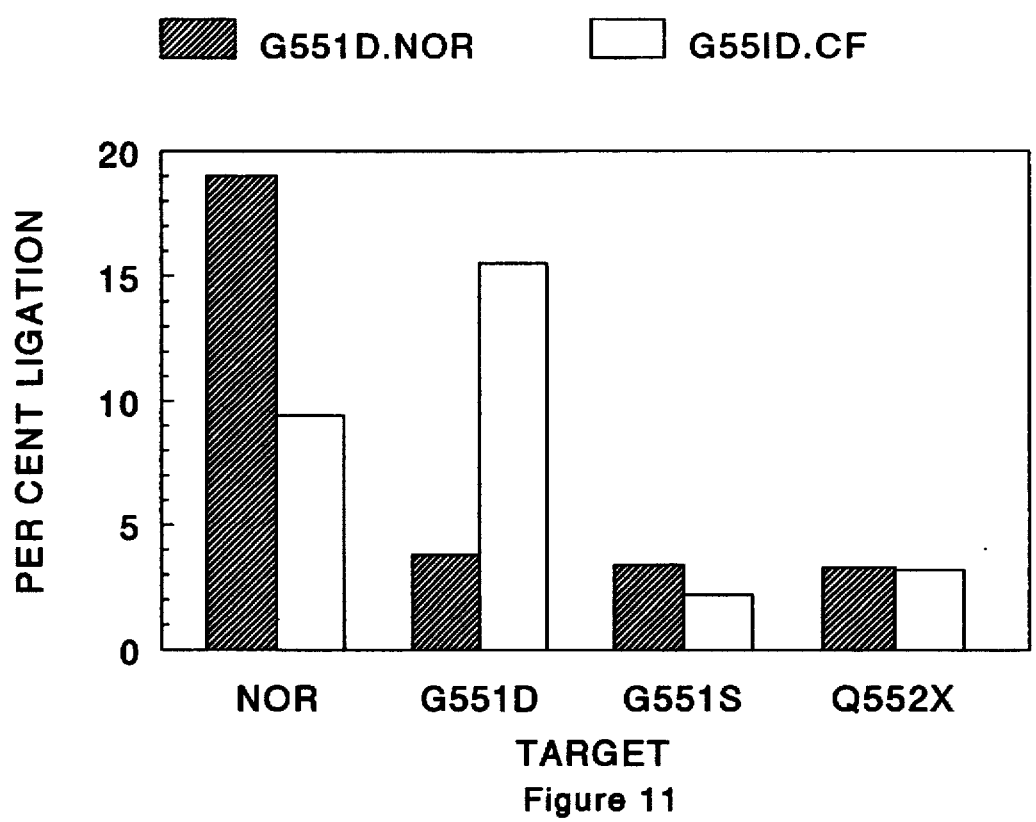
FIG. 11: HLM with $^{32}$P-G551D.NOR and $^{32}$P-G551D.CF using T4 DNA ligase with 600 mM NaCl.
Figure 12:
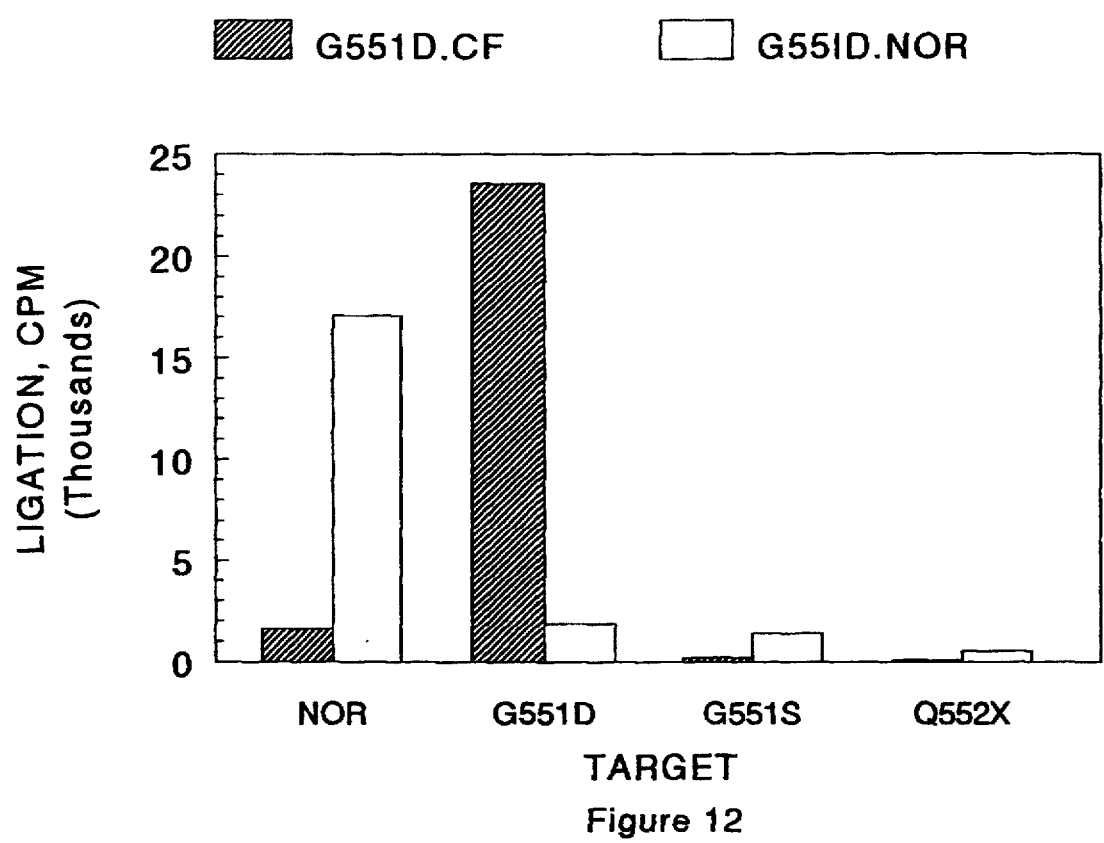
FIG. 12: Discrimination of normal, G551D, G551S, and Q552X sequences by HLM with $^{32}$P-G551D.CF or $^{32}$P-G551D.NOR using Taq DNA ligase with 200 mM KCl.
Figure 13:
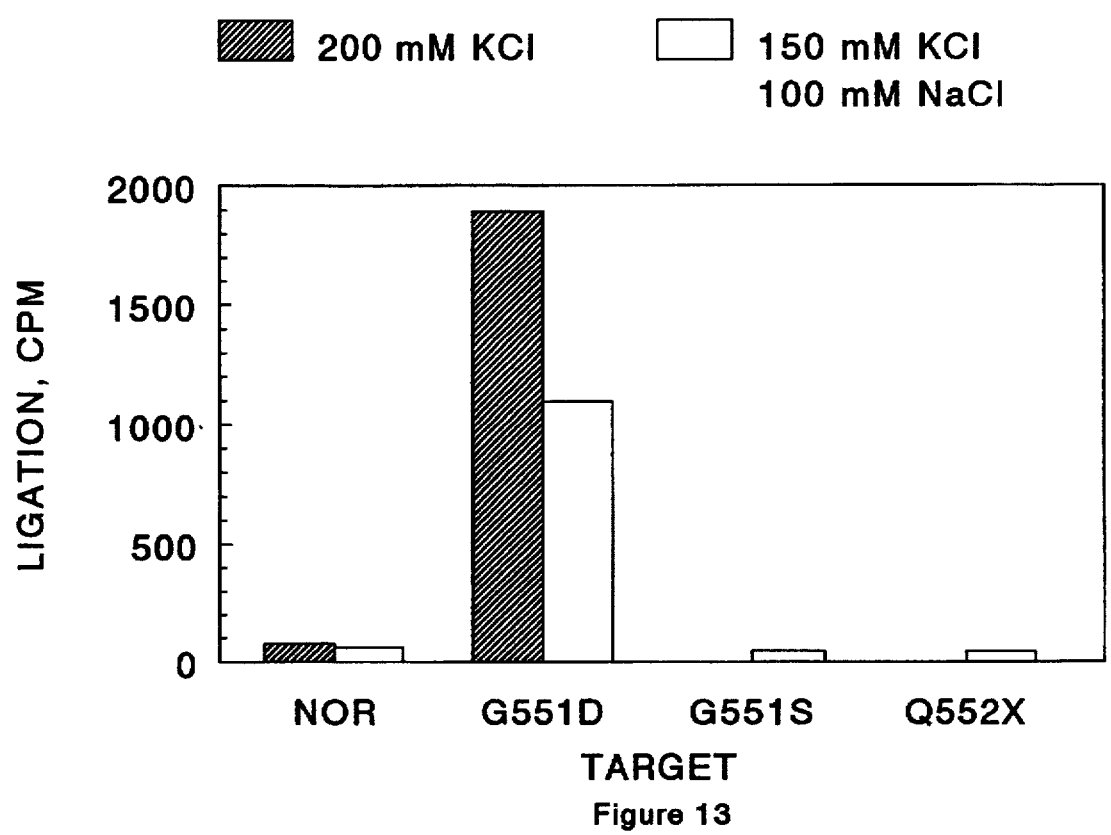
FIG. 13: Comparison of assays for G551D with Taq DNA ligase under different salt conditions.

The results of HLM analysis using the T4 DNA ligase protocol with 200 mM NaCl are shown in FIG. 10. Although HLM discriminated between the G551D sequence and the sequences for the other mutations, there was essentially no discrimination between the G551D sequence and the normal sequence with the G551D.CF probe. The specifity for HLM using T4 DNA ligase was improved by increasing the NaCl concentration to 600 mM (FIG. 11). Even better discrimination was obtained by employing HLM with Taq DNA ligase (FIG. 12), under these conditions the different sequences were readily discriminated with either G551D.CF or G551D.NOR probes. Using the the Taq DNA ligase protocol with 200 mM KCl and G551D.CF, discrimination was readily apparent between the G551D and normal sequences, but some ligation above background was observed with the normal target. This signal was able to be depressed further by substitution of NaCl into the Taq DNA ligase protocol (FIG. 13).

Taken together these results indicate the ability to HLM to discriminate sequences which differ by only a single base, even when the site of the single base change occurs at positions removed from the ligation junction.

EXAMPLE 6
Systematic Evaluation of the Specificity of Hybridization-Ligation Utilizing a p53 Model.

The preceding examples have establish the ability of HLM to discriminate sequences with subtle differences including deletions, insertions, and point mutations. In each of the cases examined conditions were established which permitted the specificity of ligation to discriminate these sequence differences. In this example, the specificity of HLM is systematically evaluated by testing its ability to discriminate sequences which differ by all of the possible combinations of mismatches.

The p53 gene codes for a protein which functions as a tumor suppressor. Mutations in this gene are observed in a wide variety of tumors, the most frequent positons for theses mutations cluster about codons 175, 245, and 248. A portion of the p53 gene surrounding codon 175 (SEQ ID NO 23) was chosen as the model for the systematic evaluation of the specificity of ligation. The target and probe sequences for this model are shown in FIG. 14. Hybridization and ligations were carried out in solution. For assays utilizing T4 DNA ligase, probes ($^{32}$P-SEQ ID NO 24 and 25) were mixed with targets in ligation buffer containing the indicated NaCl concentration. Reactions were incubated at 37° C. for 15 min, T4 DNA ligase (1 U) added and reactions incubated at 37° C. for a further 15 min. An aliquot of the reactions was analyzed by denaturing (8 M urea) polyacrylamide (15%) gel electrophoresis. Bands corresponding to the ligation product and the unligated oligomer were excised and counted by liquid scintillation counting, and the per cent of the total oligomer ligated calculated. The assays utilizing Taq DNA ligase were carried out similarly except that the ligase was added at the start of the reactions.

The ability of T4 DNA ligase to discriminate mismatches occurring at the 5' phosphate or 3' OH nucleotide at the ligation junction in 200 mM NaCl is summarized in Table II. Mismatches at the 3' OH nucleotide were much more easily discriminated than mismatches at the 5'P nucleotide. Increasing the NaCl concentration to 600 mM improved the specificity of T4 DNA ligase over that observed at 200 mM. At 600 mM NaCl, all possible mismatches at either the 5' P or 3' OH positions were discriminated, even the G-T and C-A mismatches (Table III).

The specificity of Taq DNA ligase at 45° C. in 200 mM KCl was better than that of T4 DNA ligase (Table IV). Inclusion of NaCl in the Taq ligase buffer also improved the specificity of Taq DNA ligase somewhat (Table V).

TABLE II

SPECIFICITY OF T4 DNA LIGASE IN 200 mM NaCl*

|      | 3' OH PROBE BASE | | | | 5' P PROBE BASE | | | |
|------|---|---|---|---|---|---|---|---|
| BASE | C | T | A | G | C | T | A | G |
| G    | 80 | 51 | 1.9 | 9.8 | 52 | 41 | 15 | 31 |
| A    | 20 | 72 | 1.4 | 3.6 | 58 | 65 | 45 | 15 |
| T    | 2.2 | 4.2 | 77 | 8.7 | 56 | 54 | 62 | 64 |
| C    | 1.4 | 11 | 53 | 69 | 10 | 21 | 29 | 40 |

*The results summarized in the table represent the percentages of the total amount of the limiting probe which was ligated as determined by PAGE analysis. The table is arranged so that the complementary pairs of nucleotides fall on the diagonal, the off-diagonal entries are the possible combinations of mismatches. Refer to FIG. 14 for the sequence of the hybridis formed between probes and targets.

TABLE III

SPECIFICITY OF T4 DNA LIGASE IN 600 mM NaCl*

| TARGET | 3' OH PROBE BASE | | | | 5' P PROBE BASE | | | |
|------|---|---|---|---|---|---|---|---|
| BASE | C | T | A | G | C | T | A | G |
| G | 54 | 1.1 | 0.7 | 1.5 | 36 | 17 | 1.4 | 0.7 |
| A | 2.2 | 64 | 1.0 | 3.6 | 3.0 | 31 | 1.3 | 1.0 |
| T | 1.1 | 1.3 | 55 | 2.0 | 1.6 | 14 | 43 | 37 |
| C | 1.1 | 1.1 | 1.1 | 44 | 0.6 | 2.0 | 2.5 | 25 |

*The results summarized in the table represent the percentages of the total amount of the limiting probe which was ligated as determined by PAGE analysis. The table is arranged so that the complementary pairs of nucleotides fall on the diagonal, the off-diagonal entries are the possible combinations of mismatches. Refer to FIG. 14 for the sequence of the hybridis formed between probes and targets.

TABLE IV

SPECIFICITY OF Taq DNA LIGASE IN 200 mM KCl*

| TARGET | 3' OH PROBE BASE | | | | 5' P PROBE BASE | | | |
|------|---|---|---|---|---|---|---|---|
| BASE | C | T | A | G | C | T | A | G |
| G | 60 | 8.2 | 0.6 | 1.8 | 34 | 14 | 0.6 | 1.9 |
| A | 0.8 | 64 | 1.1 | 2.6 | 7.0 | 43 | 5.0 | 3.0 |
| T | 1.5 | 2.7 | 71 | 3.3 | 5.0 | 16 | 43 | 11 |
| C | 2.7 | 2.0 | 1.6 | 61 | 2.0 | 4.0 | 11 | 34 |

*The results summarized in the table represent the percentages of the total amount of the limiting probe which was ligated as determined by PAGE analysis. The table is arranged so that the complementary pairs of nucleotides fall on the diagonal, the off-diagonal entries are the possible combinations of mismatches. Refer to FIG. 14 for the sequence of the hybridis formed between probes and targets.

TABLE V

SPECIFICITY OF Taq DNA LIGASE IN 25 mM KCl/75 mM NaCl*

|  | 3' OH PROBE BASE | | | |
|---|---|---|---|---|
| TARGET BASE | C | T | A | G |
| G | 31 | 0.6 | 0.7 | 0.7 |
| A | 1.5 | 46 | 0.7 | 2.5 |
| T | 0.8 | 2.5 | 51 | 1.7 |
| C | 0.8 | 0.8 | 0.8 | 39 |

TABLE V-continued

SPECIFICITY OF Taq DNA LIGASE IN 25 mM KCl/75 mM NaCl*

| | 3' OH PROBE BASE | | | |
|---|---|---|---|---|
| TARGET BASE | C | T | A | G |

*The results summarized in the table represent the percentages of the total amount of the limiting probe which was ligated as determined by PAGE analysis. The table is arranged so that the complementary pairs of nucleotides fall on the diagonal, the off-diagonal entries are the possible combinations of mismatches. Refer to FIG. 14 for the sequence of the hybridis formed between probes and targets.

EXAMPLE 7

Assays for the delta F-508 and Normal Alleles in PCR Amplified Human DNA Using Percent Ligation as Diagnostic Criterion Samples of PCR amplified human DNA were received from an independent laboratory. HLM analysis of the delta F-508 (SEQ ID NO 1) and normal (SEQ ID NO 2) alleles was performed as described in the previous examples. At the denaturation step to remove the hybridized but unligated probe, the supernatant containing this released probe was reserved and flashed separately, in addition to flashing the PMP which contained the hybridized and ligated labeled probe. The sum of the chemiluminescent signals from the supernatant and PMP provides a measure of the total amount of labeled probe which hybridized to the sample. This in turn provides a measure of the total amount of sample DNA in the reaction. In addition, the chemiluminescent signal from the PMP divided by the sum of the chemiluminescent signals from the supernatant and PMP provides a measure of the fraction of the hybridized probe which was ligated. Since the amount of PCR product obtained from each sample of human DNA may vary from sample to sample, the fraction of labeled probe ligated provides a clearer distinction between samples which are homozygous for an allele, samples which are heterozygous for an allele, and those which do not contain the allele. In addition, since the probes may be expected to hybridize to delta F-508, normal, and delta I-507 alleles, determining the chemiluminescence of the labeled probe released at the denaturation step, provides a means to determine that the assay components are functioning properly for those samples which are ligation negative.

Figure 15:
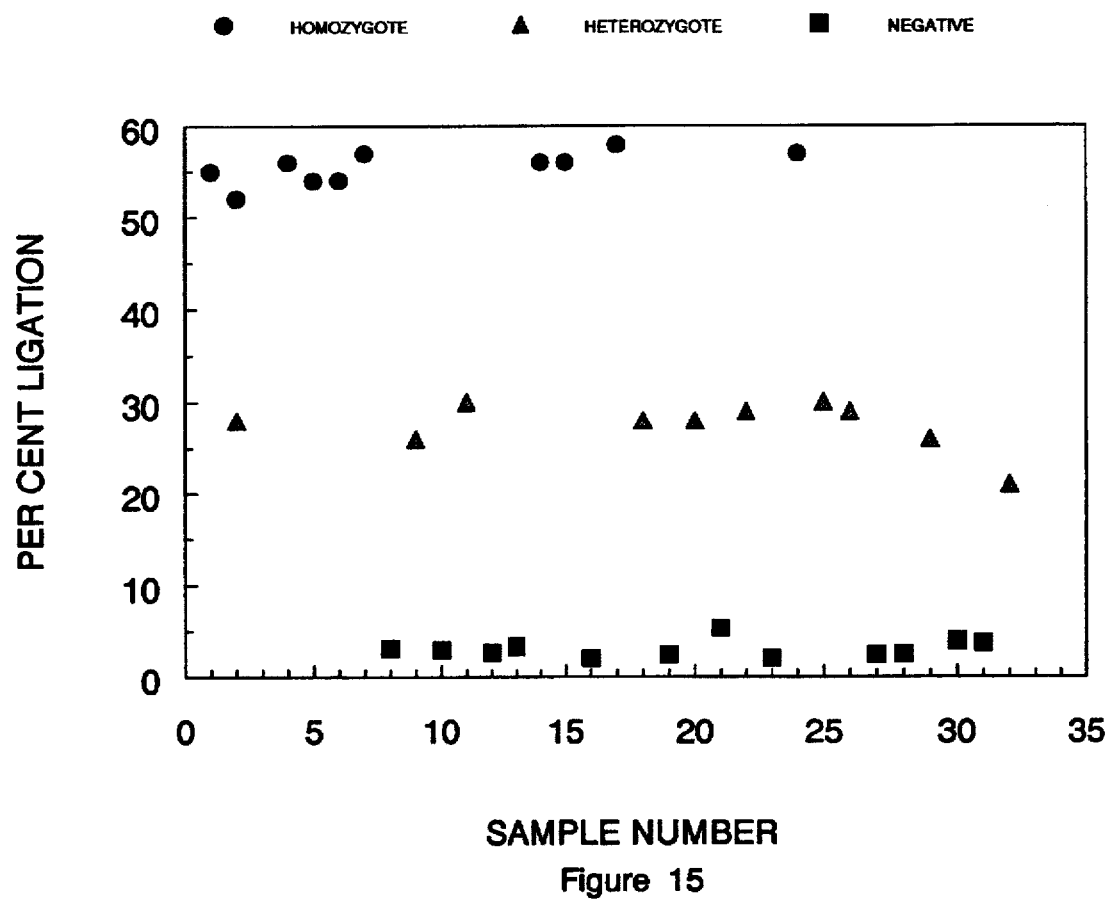
FIG. 15: Calculated per cent ligation for the delta F-508 assay of PCR amplified samples.
Figure 16:
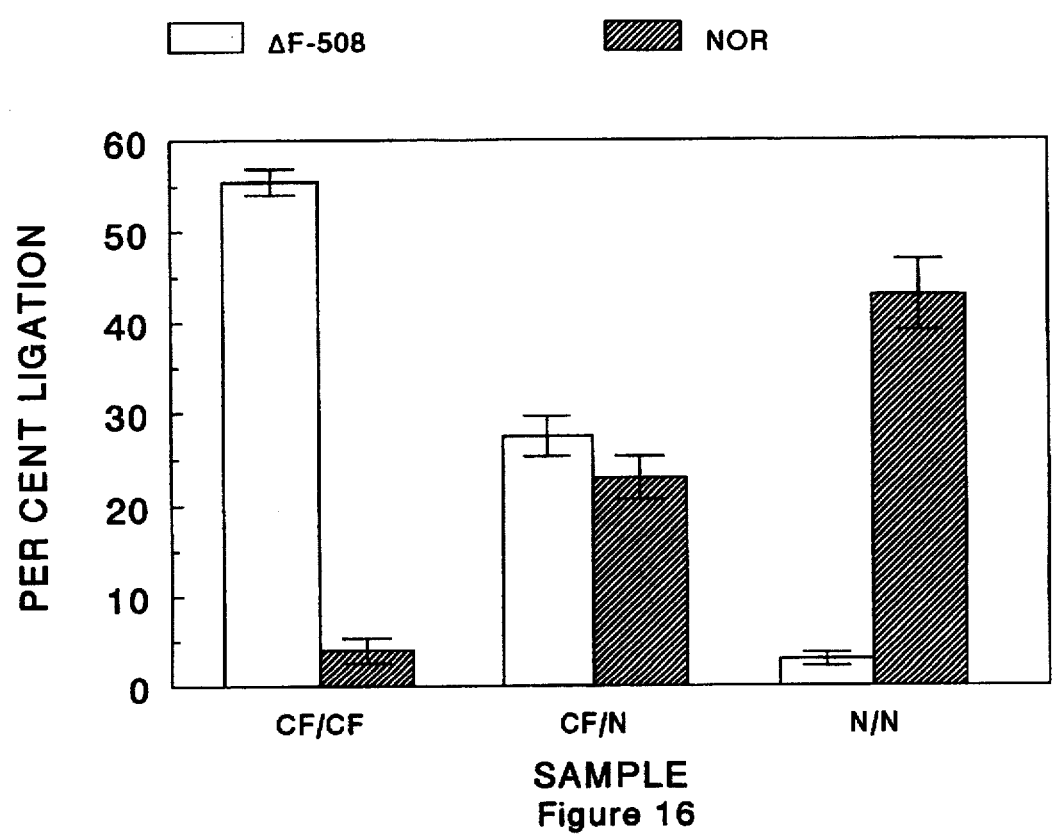
FIG. 16: The correlation of per cent ligation calculated from HLM with the genotype of PCR amplified human DNA. The error bars represent the 99% confidence interval.

The HLM results for the delta F-508 assay calculated as per cent ligation are summarized in FIG. 15. A clear discrimination between homozygous, heterozygous, and negative samples could be made based upon the calculated percentage of the labeled probe ligated. This calculated parameter turns out to be a more reliable diagnostic index than the raw chemiluminescent data because the samples were found to vary more than 5-fold in the total amount of DNA present (data not shown). In FIG. 16, similar HLM results for the assay for the normal allele are compared with those of the delta F-508 assay.

EXAMPLE 8

Effect of NaCl Concentration on the Discrimination of Delta F-508 and Delta I-507 Alleles The sequences for these two alleles differ at a single position. (See FIG. 4). Using HLM with T4 DNA ligase in 200 mM NaCl, it was possible to discriminate between these two cystic fibrosis mutations (See Examples 1 and 2). In light of the results in Example 6 showing the effect of NaCl concentration of the specificity of T4 DNA ligase with the p53 sequences, the effect of NaCl concentration on the ability of the T4 DNA ligase to discriminate between the delta F-508 and delta I-507 sequences using the delta F-508 probes was examined. HLM was performed on delta F-508 and delta I-507 synthetic target sequences as described except that ligation buffers were made up with either 200, 400, 600, 800, or 1000 mM NaCl. At the denaturation step, the supernatant was reserved and flashed separately in order to determine the amount of hybridized but unligated probe. The percentage of the 508.CF-DMAE probe which had been ligated out of the total amount hybridized was calculated as described in Example 7.

Figure 17:
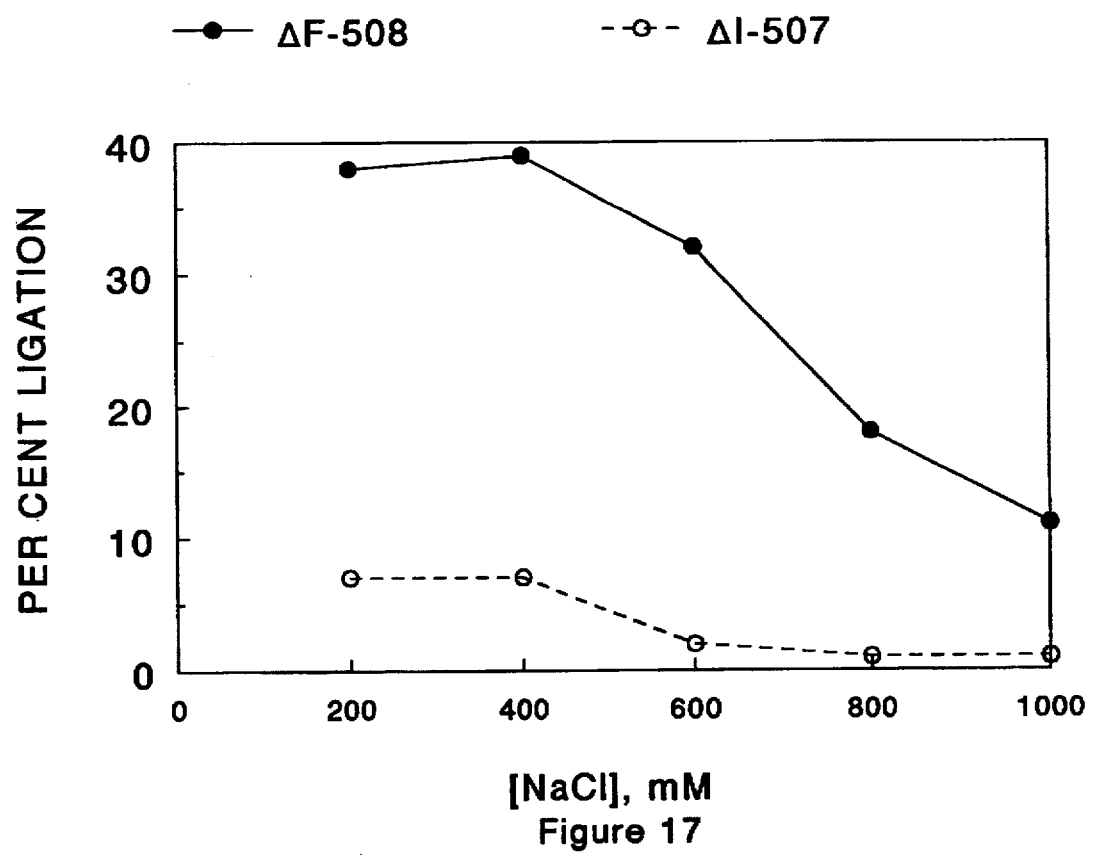
FIG. 17: Discrimination of the delta F-508 and delta I-507 sequences with delta F-508 probes by T4 DNA ligase as a function of NaCl concentration.

The results are summarized in FIG. 17. There was sufficient discrimination by T4 DNA ligase in 200 mM NaCl to distinguish between the delta F-508 and delta I-507 sequencers. Increasing the salt concentration up to 600 mM improved the discrimination between these sequences by suppressing the amount of ligation observed with the delta I-507 sequence while the maintaining the level of ligation with the delta F-508 sequence. At NaCl concentrations above 600 mM, the ligation with the delta F-508 target begins to decline.

SEQUENCE LISTING ( 1 ) GENERAL INFORMATION:

( i i i ) NUMBER OF SEQUENCES: 25

( 2 ) INFORMATION FOR SEQ ID NO: 1:

( i ) SEQUENCE CHARACTERISTICS:
        ( A ) LENGTH: 47 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: Delta F508, a portion of the sequence of
            exon 10 of the CFTR gene surrounding base number 1652
            with base 16

( x i ) SEQUENCE DESCRIPTION: SEQ ID NO: 1:

GGC ACC ATT AAA GAA AAT ATC ATT GGT GTT TCC TAT GAT GAA TAT AG    47

( 2 ) INFORMATION FOR SEQ ID NO: 2:

( i ) SEQUENCE CHARACTERISTICS:
        ( A ) LENGTH: 50 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: Normal, a portion of the sequence of
            exon 10 of the CFTR gene surrounding base number 1652

( x i ) SEQUENCE DESCRIPTION: SEQ ID NO: 2:

GGC ACC ATT AAA GAA AAT ATC ATC TTT GGT GTT TCC TAT GAT GAA    45

TAT AG    50

( 2 ) INFORMATION FOR SEQ ID NO: 3:

( i ) SEQUENCE CHARACTERISTICS:
        ( A ) LENGTH: 24 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: C16B, bases 1611 - 1634 of exon 10 of
            the CFTR gene ( x i ) SEQUENCE DESCRIPTION: SEQ ID NO: 3:

G TTT TCC TGG ATT ATG CCT GGC AC    24

( 2 ) INFORMATION FOR SEQ ID NO: 4:

( i ) SEQUENCE CHARACTERISTICS:
        ( A ) LENGTH: 24 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: C16D, bases 1708 - 1684 of exon 10 of
            the CFTR gene ( x i ) SEQUENCE DESCRIPTION: SEQ ID NO: 4:

GTT GGC ATG CTT TGA TGA CGC TTC    24

( 2 ) INFORMATION FOR SEQ ID NO: 5:

( i ) SEQUENCE CHARACTERISTICS:
        ( A ) LENGTH: 53 bases
        ( B ) TYPE: Nucleic acid
        ( C ) STRANDEDNESS: Single
        ( D ) TOPOLOGY: Linear ( i i ) MOLECULE TYPE: Other DNA/Genomic DNA
        ( A ) DESCRIPTION: PMP508, bases 1 - 29 is a spacer of
            synthetic DNA; bases 30 - 53 consists of bases 1656
            1678 of exon 10 of the CFTR gene ( x i ) SEQUENCE DESCRIPTION: SEQ ID NO: 5:

CCTAGTCCAA GTACGGCGCC GAAGAGGCC CT ATA TTC ATC ATA GGA    46

AAC ACC A    53

( 2 ) INFORMATION FOR SEQ ID NO: 6:

( i ) SEQUENCE CHARACTERISTICS:
        ( A ) LENGTH: 24 bases ( B ) TYPE: Nucleic acid
( C ) STRANDEDNESS: Single
( D ) TOPOLOGY: Linear ( i i ) MOLECULE TYPE: Genomic DNA
( A ) DESCRIPTION: 508.CF, bases 1629- 1652 of exon 10 of
the CFTR gene ( x i ) SEQUENCE DESCRIPTION: SEQ ID NO: 6:

AT GAT ATT TTC TTT AAT GGT GCC A                      24

( 2 ) INFORMATION FOR SEQ ID NO: 7:

( i ) SEQUENCE CHARACTERISTICS:
( A ) LENGTH: 27 bases
( B ) TYPE: Nucleic acid
( C ) STRANDEDNESS: Single
( D ) TOPOLOGY: Linear ( i i ) MOLECULE TYPE: Genomic DNA
( A ) DESCRIPTION: 508.NOR, bases 1629-1655 of exon 10 of
the CFTR gene ( x i ) SEQUENCE DESCRIPTION: SEQ ID NO: 7:

AA GAT GAT ATT TTC TTT AAT GGT GCC A                  27

( 2 ) INFORMATION FOR SEQ ID NO: 8:

( i ) SEQUENCE CHARACTERISTICS:
( A ) LENGTH: 47 bases
( B ) TYPE: Nucleic acid
( C ) STRANDEDNESS: Single
( D ) TOPOLOGY: Linear ( i i ) MOLECULE TYPE: Genomic DNA
( A ) DESCRIPTION: Delta I-507, a portion of the sequence
of exon 10 of the CFTR gene surrounding base number ( x i ) SEQUENCE DESCRIPTION: SEQ ID NO: 8:

GGC ACC ATT AAA GAA AAT ATC TTT GGT GTT TCC TAT GAT GAA    42

TAT AG                                                      47

( 2 ) INFORMATION FOR SEQ ID NO: 9:

( i ) SEQUENCE CHARACTERISTICS:
( A ) LENGTH: 56 bases
( B ) TYPE: Nucleic acid
( C ) STRANDEDNESS: Single
( D ) TOPOLOGY: Linear ( i i ) MOLECULE TYPE: Genomic DNA / other DNA
( A ) DESCRIPTION: PMP.507: bases 1 - 29 is a spacer of
synthetic DNA; bases 30 - 56 consists of bases
1679 - 1653 of exon 10 of the CFTR gene ( x i ) SEQUENCE DESCRIPTION: SEQ ID NO: 9:

CCTAGTCCAA GTACGGCGCC GAAGAGGCC CT ATA TTC ATC ATA GGA    46

AAC ACC AAA G                                              56

( 2 ) INFORMATION FOR SEQ ID NO: 10:

( i ) SEQUENCE CHARACTERISTICS:
( A ) LENGTH: 24 bases
( B ) TYPE: Nucleic acid
( C ) STRANDEDNESS: Single
( D ) TOPOLOGY: Linear ( i i ) MOLECULE TYPE: Genomic DNA
( A ) DESCRIPTION: 507.CF, consists of bases 1626-1649 of
exon 10 of the CFTR gene ( x i ) SEQUENCE DESCRIPTION: SEQ ID NO: 10:

AT ATT TTC TTT AAT GGT GCC AGG C                                    24

( 2 ) INFORMATION FOR SEQ ID NO: 11:

( i ) SEQUENCE CHARACTERISTICS:
        ( A ) LENGTH: 54 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: G542X, bases 1731 - 1784 of exon 11 of
            the CFTR gene with T substituted for G at base 1756

( x i ) SEQUENCE DESCRIPTION: SEQ ID NO: 11:

T GCA GAG AAA GAC AAT ATA GTT CTT TGA GAA GGT GGA ATC ACA CTG       46

AGT GGA GG                                                          54

( 2 ) INFORMATION FOR SEQ ID NO: 12:

( i ) SEQUENCE CHARACTERISTICS:
        ( A ) LENGTH: 54 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: NOR1731.54, bases 1731 - 1784 of exon 11
            of the CFTR gene ( x i ) SEQUENCE DESCRIPTION: SEQ ID NO: 12:

T GCA GAG AAA GAC AAT ATA GTT CTT GGA GAA GGT GGA ATC ACA CTG       46

AGT GGA GG                                                          54

( 2 ) INFORMATION FOR SEQ ID NO: 13:

( i ) SEQUENCE CHARACTERISTICS:
        ( A ) LENGTH: 52 bases
        ( B ) TYPE: Nucleic acid
        ( C ) STRANDEDNESS: Single
        ( D ) TOPOLOGY: Linear ( i i ) MOLECULE TYPE: Other DNA/Genomic DNA
        ( A ) DESCRIPTION: PMP.G542X, bases 1- 27 consists of a
            spacer of synthetic DNA, bases 28 - 51 consists of
            bases 1781- 1757 of exon 11 of the CFTR gene ( x i ) SEQUENCE DESCRIPTION: SEQ ID NO: 13:

CCTAGTCCAA GTACGGCGCC GAAGAGGCC ACT CAG TGT GAT TCC ACC             47

TTC TC                                                              52

( 2 ) INFORMATION FOR SEQ ID NO: 14:

( i ) SEQUENCE CHARACTERISTICS:
        ( A ) LENGTH: 27 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: G542X.CF, bases 1756 - 1730 of exon 11
            of the CFTR gene with T substituted for C at base
            1756

( x i ) SEQUENCE DESCRIPTION: SEQ ID NO: 14:

A AAG AAC TAT ATT GTC TTT CTC TGC AA                                27

( 2 ) INFORMATION FOR SEQ ID NO: 15:

( i ) SEQUENCE CHARACTERISTICS:
        ( A ) LENGTH: 27 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: G542X.NOR, bases 1756 - 1730 of exon 11
            of the CFTR gene ( x i ) SEQUENCE DESCRIPTION: SEQ ID NO: 15:

CAA GAA CTA TAT TGT CTT TCT CTG CAA                            27

( 2 ) INFORMATION FOR SEQ ID NO: 16:

( i ) SEQUENCE CHARACTERISTICS:
        ( A ) LENGTH: 45 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: G551D, bases 1763 - 1807 of exon 11 of
            the CFTR gene with A substituted for the G at base
            1784

( x i ) SEQUENCE DESCRIPTION: SEQ ID NO: 16:

GT GGA ATC ACA CTG AGT GGA GAT CAA CCA GCA AGA ATT TCT TTA G       45

( 2 ) INFORMATION FOR SEQ ID NO: 17:

( i ) SEQUENCE CHARACTERISTICS:
        ( A ) LENGTH: 45 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: NOR17632.45, bases 1763 - 1807 of exon
            11 of the CFTR gene ( x i ) SEQUENCE DESCRIPTION: SEQ ID NO: 17:

GT GGA ATC ACA CTG AGT GGA GGT CAA CCA GCA AGA ATT TCT TTA G       45

( 2 ) INFORMATION FOR SEQ ID NO: 18:

( i ) SEQUENCE CHARACTERISTICS:
        ( A ) LENGTH: 45 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: G551S, bases 1763 - 1807 of exon 11 of
            the CFTR gene with A substituted for G at base 1783

( x i ) SEQUENCE DESCRIPTION: SEQ ID NO: 18:

GT GGA ATC ACA CTG AGT GGA AGT CAA CCA GCA AGA ATT TCT TTA G       45

( 2 ) INFORMATION FOR SEQ ID NO: 19:

( i ) SEQUENCE CHARACTERISTICS:
        ( A ) LENGTH: 45 bases
        ( B ) TYPE: Nucleic Acid
        ( C ) STRANDEDNESS: Single
        ( D ) TOPOLOGY: Linear ( i i ) MOLECULE TYPE: Genomic DNA ( A ) DESCRIPTION: Q552X, bases 1763 - 1807 of exon 11 of
the CFTR gene with T substituted for C at base 1786

( x i ) SEQUENCE DESCRIPTION: SEQ ID NO: 19:

GT GGA ATC ACA CTG AGT GGA GGT TAA CCA GCA AGA ATT TCT TTA G    45

( 2 ) INFORMATION FOR SEQ ID NO: 20:

( i ) SEQUENCE CHARACTERISTICS:
        ( A ) LENGTH: 52 bases
        ( B ) TYPE: Nucleic acid
        ( C ) STRANDEDNESS: Single
        ( D ) TOPOLOGY: Linear ( i i ) MOLECULE TYPE: Other DNA/Genomic DNA
        ( A ) DESCRIPTION: PMP.G551D, bases 1- 29 consist of a
            1785 - 1807 of exon 11 of the CFTR gene ( x i ) SEQUENCE DESCRIPTION: SEQ ID NO: 20:

CCTAGTCCAA GTACGGCGCC GAAGAGGCC C TAA AGA AAT TCT TGC    45

TCG TTG A    52

( 2 ) INFORMATION FOR SEQ ID NO: 21:

( i ) SEQUENCE CHARACTERISTICS:
        ( A ) LENGTH: 22 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: G551D.CF, bases 1784 - 1763 of exon 11
            of the CFTR gene with T substituted for C at base
            1784

( x i ) SEQUENCE DESCRIPTION: SEQ ID NO: 21:

TC TCC ACT CAG TGT GAT TCC AC    22

( 2 ) INFORMATION FOR SEQ ID NO: 22:

( i ) SEQUENCE CHARACTERISTICS:
        ( A ) LENGTH: 22 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: G551D.NOR, bases 1784-1763 of exon 11 of
            the CFTR gene ( x i ) SEQUENCE DESCRIPTION: SEQ ID NO: 22:

CC TCC ACT CAG TGT GAT TCC AC    2

( 2 ) INFORMATION FOR SEQ ID NO: 23:

( i ) SEQUENCE CHARACTERISTICS:
        ( A ) LENGTH: 35 bases
        ( B ) TYPE: Nucleic acid
        ( C ) STRANDEDNESS: Single
        ( D ) TOPOLOGY: Linear ( i i ) MOLECULE TYPE: Genomic DNA
        ( A ) DESCRIPTION: p53, 35 bases flanking codon 175 of the
            gene for p53

( x i ) SEQUENCE DESCRIPTION: SEQ ID NO: 23:

ATG AGG GAG GTT GTG AGG CGC TGC CCC CAC CAT GA    35

( 2 ) INFORMATION FOR SEQ ID NO: 24:

```
        ( i ) SEQUENCE CHARACTERISTICS:
                ( A ) LENGTH: 16 bases
                ( B ) TYPE: Nucleic acid
                ( C ) STRANDEDNESS: Single
                ( D ) TOPOLOGY: Linear ( i i ) MOLECULE TYPE: Genomic DNA
                ( A ) DESCRIPTION: p53.5', The sequence of 16 bases
                        extending 5'from the C of codon 175 of
                        the p53 gene.

( x i ) SEQUENCE DESCRIPTION: SEQ ID NO: 24:

T C   A T G   G T G   G G G   G C A   G C                                                    1 6

( 2 ) INFORMATION FOR SEQ ID NO: 25:

( i ) SEQUENCE CHARACTERISTICS:
                ( A ) LENGTH: 19 bases
                ( B ) TYPE: Nucleic acid
                ( C ) STRANDEDNESS: Single
                ( D ) TOPOLOGY: Linear ( i i ) MOLECULE TYPE: Genomic DNA
                ( A ) DESCRIPTION: p53.3', The sequence of 19 bases
                        extending 3'from the G of codon 175 of
                        the p53 gene.

( x i ) SEQUENCE DESCRIPTION: SEQ ID NO: 25:

G   C C T   C A C   A A C   C T C   C C T   C A T                                             1 9
```

What is claimed is:

1. A method for identifying a target polynucleic acid sequence in a reaction mixture, by detecting whether or not a label is present comprising:
   a) selecting a first probe and a second probe, such that
      i) they are each complementary to a sufficient portion of the target to permit the formation of a hybrid,
      ii) the first probe is joined to a moiety which is a means for selectively separating the first probe from the reaction mixture,
      iii) the second probe is joined to a label or means for selectively attaching a label,
   b) mixing the probes with the target polynucleic acid in such a manner that the probes will hybridize under high stringency conditions specifically to the target polynucleic acid,
   c) adding a ligating reagent,
   d) denaturing the hybridized probes and target polynucleic acid in the reaction mixture so that the probes will be separated from the target polynucleic acid,
   e) separating the first probe from the reaction mixture, utilizing the moiety that permits selective separation, and
   f) analyzing the selectively separated first probe to determine if the label, or means for attaching a label, of the second probe is present, whereby the identification of the target polynucleotide sequence is made, by correlating the presence or absence of label or means for attaching the label on the second probe with the presence or absence of the target polynucleotide, and analyzing the supernatant remaining after separation of the first probe to determine the amount of label present therein and, further, to determine the percent of hybridized labeled probe which has been ligated to said first probe,
   wherein a step for separating the hybridized probes and target, utilizing the moiety that permits selective separation, must take place either (1) before ligating step c), (2) after ligating step c), or (3) both before and after ligating step c).

2. The method of claim 1 wherein the moiety that permits the first probe to be selectively separated is an insoluble particle.

3. The method of claim 1 wherein the moiety that permits the probe to be selectively separated is a magnetic particle.

4. The method of claim 1 wherein the label is selected from the group consisting of enzymatic moieties, radioactive moieties, fluorescent moieties, and luminescent moieties.

5. The method of claim 1 wherein said means for selectively attaching a label is avidin or biotin.

6. The method of claim 4 wherein the label is a luminescent material.

7. The method of claim 6 wherein the label is an acridinium ester.

8. The method of claim 1 in which the label is an acridinium ester and the analysis of the selectively separated probe to determine the presence of label comprises the addition of DNAase before addition of a flash reagent which triggers the release of detectable signal from the acridinium ester.

9. The method of claim 1 wherein the target polynucleic acid is selected from the group consisting of DNA, RNA, and viral nucleic acids.

10. The method of claim 1 which also includes a step for amplifying the target polynucleic acid before it is mixed with said probes.

11. The method of claim 10 in which the amplification technique is selected from the group consisting of polymerase chain reaction, ligase chain reaction, and QB replicase amplification.

12. The method of claim 1 in which the ligating agent acts enzymatically or chemically to join the two probes.

13. The method of claim 12 in which the ligating agent is ligase.

14. A method for identifying a target polynucleic acid sequence in a reaction mixture, by detecting whether or not a label is present comprising:
   a) selecting a first probe and a second probe, such that
      i) they are each complementary to a sufficient portion of the target to permit the formation of a hybrid,
      ii) the first probe is joined to a moiety which is a means for selectively separating the first probe from the reaction mixture,
      iii) the second probe is joined to a label or means for selectively attaching a label,
   b) mixing the probes with the target polynucleic acid in such a manner that the probes will hybridize under high stringency conditions specifically to the target polynucleic acid,
   c) adding a ligating reagent and sodium chloride, said sodium chloride being present in a concentration of greater than 200 mM and up to 1000 mM,
   d) denaturing the hybridized probes and target polynucleic acid in the reaction mixture so that the probes will be separated from the target polynucleic acid,
   e) separating the first probe from the reaction mixture, utilizing the moiety that permits selective separation, and
   f) analyzing the selectively separated first probe to determine if the label, or means for attaching a label, of the second probe is present, whereby the identification of the target polynucleotide sequence is made, by correlating the presence or absence of label or means for attaching the label on the second probe with the presence or absence of the target polynucleotide sequence, and analyzing the supernatant remaining after separation of the first probe to determine the amount of label present therein and, further, to determine the percent of hybridized labeled probe which has been ligated to said first probe,
   wherein a step for separating the hybridized probes and target, utilizing the moiety that permits selective separation, must take place either (1) before ligating step c), (2) after ligating step c), or (3) both before and after ligating step c).

15. The method of claim 14 in which the sodium chloride concentration is 500–700 mM.

16. The method of claim 15 in which the sodium chloride concentration is approximately 600 mM.

17. The method of claim 1 in which, after denaturation, the sample is passed through a chromatography column, said column being analyzed to determine if the label is attached thereto.

18. A method for identifying a target polynucleic acid sequence in a reaction mixture by detecting whether or not probes added to the reaction mixture become a continuously replicating vector having both subunits of the midivarient sequence of the QB replicase system in functional relation to each other comprising:
   a) selecting a first probe and a second probe, such that
      i) they are each complementary to a sufficient portion of the target to permit the formation of a hybrid,
      ii) the first probe is joined to a subunit of the midivariant sequence of the QB replicase system,
      iii) the second probe is joined to the second subunit midivarient sequence of the QB replicase system, different than that of the first probe,
   b) mixing the probes with the target polynucleic acid in such a manner that the probes will hybridize to the target polynucleic acid,
   c) adding a ligating reagent,
   d) optionally denaturing the hybridized probes and target polynucleic acid in the reaction mixture so that the probes will be separated from the target polynucleic acid, and
   e) placing the hybridized probes and target polynucleic acid in a second reaction mixture containing QB replicase, to determine if said hybridized probes have the ability to replicate, whereby the ability to replicate indicates the identity of the target polynucleic acid in the context of the sequence of the probes.

19. The method of claim 18 in which QB replicase is added along with the probes to the reaction mixture, and the analysis comprises determining if the probes have replicated.

20. A method for identifying the sequence of a target polynucleic acid by detecting whether the target polynucleic acid is complementary to one or more of two or more probes in a reaction mixture, by detecting whether or not a label is present comprising:
   a) selecting a first probe and a second probe and optionally additional probes such that
      i) they are each complementary to a sufficient portion of the target to permit the formation of a hybrid,
      ii) said first probe is complementary to a terminal segment of the nucleic acid sequence of the target polynucleic acid, and is joined to a moiety which is a means for selectively separating the first probe from the reaction mixture,
      iii) said second probe is complementary to a nucleic acid sequence of a terminal segment, different than that of the first probe, of the nucleic acid sequence of the target polynucleic acid, and is joined to a label or means for attaching a label,
      iv) additional probes are complementary to the nucleic acid sequence corresponding to the nucleic acid sequence of the region between the terminal segments of the target polynucleic acid of the first and second probe,
   b) mixing the probes with the target polynucleic acid in such a manner that the probes will hybridize to the target polynucleic acid, c) adding a ligating reagent, d) denaturing the hybridized probes and target polynucleic acid in the reaction mixture so that the probes will be separated from the target polynucleic acid, e) selectively separating the first probe from the reaction mixture, utilizing the moiety that permits selective separation, and f) analyzing the selectively separated probe to determine if the label, or means for attaching a label is present, whereby the identification of the target polynucleotide sequence is made, by correlating the presence or absence of label or means for attaching the label on the second probe with the presence or absence of the target polynucleotide sequence.

21. The method of claim 1 in which the label is located in such a position that it does not interfere with hybridization and ligation.

22. The method of claim 1 which also includes the process wherein, before denaturation, an aliquot is removed, said aliquot being analyzed to determine if the label is hybridized to the target by
   a) separating the first probe containing the moiety that permits separation and any hybridized target or second probe, and
   b) analyzing said separated first probe and any hybridized target and second probe to determine if the label or means for attaching a label is present.

23. The method of claim 1 which also includes analyzing the supernatant remaining after separation of said probe containing said moiety that permits separation to determine the presence of the label contained therein.

24. A method of claim 1, 13, or 18 wherein the ligating reagent is selected from the group consisting of Taq DNA-ligase or T4 DNA-ligase.

25. The method of claim 24 in which said Taq DNA ligase is in a buffer which includes tRNA.

26. The method of claim 1 wherein the second probe consists of a mixture of probes of different nucleic acid sequences, each (a) connected to a unique label or (b) being capable of attachment to said label, said label being attached before detection, whereby the detection of each unique label will allow the identification of the nucleic acid sequence of the target polynucleic acid.

27. A method for identifying a target polynucleic acid sequence in a reaction mixture, by detecting whether or not a label is present comprising:
 a) selecting a first probe and a second probe, such that
  i) they are each complementary to a sufficient portion of the target to permit the formation of a hybrid,
  ii) the first probe is joined to a moiety which is a means for selectively separating the first probe from the reaction mixture,
  iii) the second probe is joined to a label or means for selectively attaching a label,
 b) mixing the probes with the target polynucleic acid in such a manner that the probes will hybridize under high stringency conditions specifically to the target polynucleic acid,
 c) adding a ligating reagent,
 d) denaturing the hybridized probes and target polynucleic acid in the reaction mixture so that the probes will be separated from the target polynucleic acid,
 e) separating the first probe from the reaction mixture, utilizing the moiety that permits selective separation, and
 f) analyzing the selectively separated first probe to determine if the label, or means for attaching a label, of the second probe is present, whereby the identification of the target polynucleotide sequence is made, by correlating the presence or absence of label or means for attaching the label on the second probe with the presence or absence of the target polynucleotide, and analyzing the supernatant remaining after separation of the first probe to determine the amount of label present therein and, further, to determine the percent of hybridized labeled probe which has been ligated to said first probe,
 wherein a step for separating the hybridized probes and target, utilizing the moiety that permits selective separation, must take place either (1) before ligating step c), (2) after ligating step c), or (3) both before and after ligating step c), and
 wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

28. A method for identifying a target polynucleic acid sequence in a reaction mixture, by detecting whether or not a label is present comprising:
 a) selecting a first probe and a second probe, such that
  i) they would each be complementary to a sufficient portion of the target to permit the formation of a hybrid,
  ii) the first probe is joined to a moiety which is a means for selectively separating the first probe from the reaction mixture,
  iii) the second probe is joined to a label or means for selectively attaching a label,
 b) mixing the probes with the target polynucleic acid in such a manner that the probes will hybridize under high stringency conditions specifically to the target polynucleic acid.
 c) selectively separating the hybridized probes and target polynucleic acid of the prior step from the reaction mixture, utilizing the moiety that permits selective separation, and
 d) analyzing the selectively separated hybridized probes and target polynucleic acid to determine if the label, or means for attaching a label, of the second probe is present, whereby the identification of the target polynucleotide sequence, by correlating the presence or absence of label or means for attaching the label on the second probe with the presence or absence of target polynucleotide sequence,
 wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

29. A method for detecting mutation in a target DNA in a reaction mixture, by detecting whether or not a label is present comprising:
 a) selecting a first probe and a second probe, such that
  i) they would each be complementary to a sufficient portion of the target to permit the formation of a,
  ii) the first probe is joined to a moiety which is a means for selectively separating the first probe from the reaction mixture,
  iii) the second probe is joined to a label or means for selectively attaching a label,
 b) mixing the probes with the target DNA in such a manner that the probes will hybridize under high stringency conditions specifically to the target DNA,
 c) selectively separating the first probe from the reaction mixture, utilizing the moiety that permits selective separation, and
 d) analyzing the selectively separated first probe to determine if the label, or means for attaching a label, is present, and correlating the presence or absence of label with the presence or absence of mutation in the target DNA sequence,
 wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

30. A method for detecting mutation in a target DNA in a reaction mixture, by detecting whether or not a label is present comprising:

a) selecting a first probe and a second probe, such that
  i) they are each complementary to a sufficient portion of the target to permit the formation of a hybrid,
  ii) the first probe is joined to a moiety which is a means for selectively separating the first probe from the reaction mixture,
  iii) the second probe is joined to a label or means for selectively attaching a label,
b) mixing the probes with the target DNA in such a manner that the probes will hybridize under high stringency conditions specifically to the target DNA,
c) adding a ligating reagent,
d) denaturing the hybridized probes and target DNA in the reaction mixture so that the probes will be separated from the target DNA,
e) selectively separating the first probe from the reaction mixture, utilizing the moiety that permits separation, and
f) analyzing the selectively separated first probe to determine if the label, or means for attaching a label is present, whereby the presence of a mutation in the target DNA, by correlating the presence or absence of label or means for attaching the label on the second probe with the presence or absence of the target polynucleotide sequence, and analyzing the supernatant remaining after separation of the first probe to determine the amount of label present therein and, further, to determine the percent of hybridized labeled probe which has been ligated to said first probe,
wherein a step for separating the hybridized probes and target, utilizing the moiety that permits selective separation, must take place either (1) before ligating step c), (2) after ligating step c), or (3) both before and after ligating step c), and
wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

31. The method of claim 18 wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

32. The method of claim 20 wherein the second probe consists of a mixture of probes of different nucleic acid sequences, uniquely connected to a label or means for attaching a label such that each unique nucleic acid sequence is attached to a unique label or means for attaching a label, whereby the detection of each unique label will allow the identification of the nucleic acid sequence of the target polynucleic acid.

33. A method for identifying the sequence of a target polynucleic acid by detecting whether the target polynucleic acid is complementary to one or more of two or more probes in a reaction mixture, by detecting whether or not a label is present comprising:
a) selecting a first probe and a second probe and optionally additional probes, such that
  i) they are each complementary to a sufficient portion of the target to permit the formation of a hybrid,
  ii) the first probe is complementary to a terminal segment of the nucleic acid sequence of the target polynucleic acid, and is joined to a moiety which is a means for selectively separating the first probe from the reaction mixture,
  iii) the second probe is complementary to a nucleic acid sequence of a terminal segment, different than that of the first probe, of the nucleic acid sequence of the target polynucleic acid, and is joined to a label or means for attaching a label,
  iv) additional probes are complementary to the nucleic acid sequence corresponding to the nucleic acid sequence of the region between the terminal segments of the target polynucleic acid of the first and second probe,
b) mixing the probes with the target polynucleic acid in such a manner that the probes will hybridize to the target polynucleic acid,
c) adding a ligating reagent,
d) denaturing the hybridized probes and target polynucleic acid in the reaction mixture so that the probes will be separated from the target polynucleic acid,
e) selectively separating the first probe from the reaction mixture, utilizing the moiety that permits selective separation, and
f) analyzing the selectively separated probe to determine if the label, or means for attaching a label is present, whereby the identification of the target polynucleotide sequence is made, by correlating the presence or absence of label or means for attaching the label on the second probe with the presence or absence of the target polynucleotide sequence, and analyzing the supernatant remaining after separation of the first probe to determine the amount of label present therein and, further, to determine the percent of hybridized labeled probe which has been ligated to said first probe,
wherein a step for separating the hybridized probes and target, utilizing the moiety that permits selective separation, must take place either (1) before ligating step c), (2) after ligating step c), or (3) both before and after ligating step c), and
wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

34. A method for detecting mutation in a target DNA in a reaction mixture, by detecting whether or not a label is present comprising:
a) selecting a first probe and a second probe, such that
  i) they are each complementary to a sufficient portion of the target to permit the formation of a hybrid,
  ii) the first probe is joined to a moiety which is a means for selectively separating the first probe from the reaction mixture,
  iii) the second probe is joined to a label or means for selectively attaching a label,
b) mixing the probes with the target DNA in such a manner that the probes will hybridize under high stringency conditions specifically to the target DNA,
c) adding a ligating reagent and sodium chloride, said sodium chloride present in a concentration of greater than 200 mM and up to 1000 mM, d) denaturing the hybridized probes and target DNA in the reaction mixture so that the probes will be separated from the target DNA, e) selectively separating the first probe from the reaction mixture, utilizing the moiety that permits separation, and f) analyzing the selectively separated first probe to determine if the label, or means for attaching a label is present, whereby the presence of a mutation in the target DNA, in the context of the nucleic acid sequence of the probes, is determined by whether or not the label, or means for attaching a label is detected.

35. The method of claim 18 in which the sodium chloride concentration is greater than 200 mM and up to 1000 mM.

36. The method of claim 20 in which the sodium chloride concentration is greater than 200 mM and up to 1000 mM.

37. The method of claim 14 in which said sodium chloride is replaced by another salt or a mixture of salts.

38. A method for identifying a target polynucleic acid sequence in a reaction mixture, by detecting whether or not a label is present comprising:

a) selecting a first probe and a second probe, such that
i) they are each complementary to a sufficient portion of the target to permit the formation of a hybrid,
ii) the first probe is joined to a moiety which is a means for selectively separating the first probe from the reaction mixture,
iii) the second probe is joined to a label or means for selectively attaching a label, b) mixing the probes with the target polynucleic acid in such a manner that the probes will hybridize under high stringency conditions specifically to the target polynucleic acid, c) adding a ligating reagent and sodium chloride, said sodium chloride being present in a concentration of greater than 200 mM and up to 1000 mM, d) denaturing the hybridized probes and target polynucleic acid in the reaction mixture so that the probes will be separated from the target polynucleic acid, e) separating the first probe from the reaction mixture, utilizing the moiety that permits selective separation, and f) analyzing the selectively separated first probe to determine if the label, or means for attaching a label, of the second probe is present, whereby the identification of the target polynucleotide sequence is made, by correlating the presence or absence of label or means for attaching the label on the second probe with the presence or absence of the target polynucleotide, wherein a step for separating the hybridized probes and target, utilizing the moiety that permits selective separation, must take place either (1) before ligating step c), (2) after ligating step c), or (3) both before and after ligating step c).

39. A method for identifying a target polynucleic acid sequence in a reaction mixture, by detecting whether or not a label is present comprising:

a) selecting a first probe and a second probe, such that
i) they are each complementary to a sufficient portion of the target to permit the formation of a hybrid,
ii) the first probe is joined to a moiety which is a means for selectively separating the first probe from the reaction mixture,
iii) the second probe is joined to a label or means for selectively attaching a label, b) mixing the probes with the target polynucleic acid in such a manner that the probes will hybridize under high stringency conditions specifically to the target polynucleic acid, c) adding a ligating reagent, d) denaturing the hybridized probes and target polynucleic acid in the reaction mixture so that the probes will be separated from the target polynucleic acid, e) separating the first probe from the reaction mixture, utilizing the moiety that permits selective separation, and f) analyzing the selectively separated first probe to determine if the label, or means for attaching a label, of the second probe is present, whereby the identification of the target polynucleotide sequence is made, by correlating the presence or absence of label or means for attaching the label on the second probe with the presence or absence of the target polynucleotide sequence, wherein a step for separating the hybridized probes and target, utilizing the moiety that permits selective separation, must take place either (1) before ligating step c), (2) after ligating step c), or (3) both before and after ligating step c), and wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

40. A method for detecting mutation in a target DNA in a reaction mixture, by detecting whether or not a label is present comprising:

a) selecting a first probe and a second probe, such that
i) they are each complementary to a sufficient portion of the target to permit the formation of a hybrid,
ii) the first probe is joined to a moiety which is a means for selectively separating the first probe from the reaction mixture,
iii) the second probe is joined to a label or means for selectively attaching a label, b) mixing the probes with the target DNA in such a manner that the probes will hybridize under high stringency conditions specifically to the target DNA, c) adding a ligating reagent, d) denaturing the hybridized probes and target DNA in the reaction mixture so that the probes will be separated from the target DNA, e) selectively separating the first probe from the reaction mixture, utilizing the moiety that permits separation, and f) analyzing the selectively separated first probe to determine if the label, or means for attaching a label is present, whereby the presence of a mutation in the target DNA, by correlating the presence or absence of label or means for attaching the label on the second probe with the presence or absence of the target polynucleotide sequence, wherein a step for separating the hybridized probes and target, utilizing the moiety that permits selective separation, must take place either (1) before ligating step c), (2) after ligating step c), or (3) both before and after ligating step c), and wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

41. A method for identifying the sequence of a target polynucleic acid by detecting whether the target polynucleic acid is complementary to one or more of two or more probes in a reaction mixture, by detecting whether or not a label is present comprising:

a) selecting a first probe and a second probe and optionally additional probes, such that
  i) they are each complementary to a sufficient portion of the target to permit the formation of a hybrid,
  ii) the first probe is complementary to a terminal segment of the nucleic acid sequence of the target polynucleic acid, and is joined to a moiety which is a means for selectively separating the first probe from the reaction mixture,
  iii) the second probe is complementary to a nucleic acid sequence of a terminal segment, different than that of the first probe, of the nucleic acid sequence of the target polynucleic acid, and is joined to a label or means for attaching a label,
  iv) additional probes are complementary to the nucleic acid sequence corresponding to the nucleic acid sequence of the region between the terminal segments of the target polynucleic acid of the first and second probe,
b) mixing the probes with the target polynucleic acid in such a manner that the probes will hybridize to the target polynucleic acid,
c) adding a ligating reagent,
d) denaturing the hybridized probes and target polynucleic acid in the reaction mixture so that the probes will be separated from the target polynucleic acid,
e) selectively separating the first probe from the reaction mixture, utilizing the moiety that permits selective separation, and
f) analyzing the selectively separated probe to determine if the label, or means for attaching a label is present, whereby the identification of the target polynucleotide sequence is made, by correlating the presence or absence of label or means for attaching the label on the second probe with the presence or absence of the target polynucleotide sequence, wherein a step for separating the hybridized probes and target, utilizing the moiety that permits selective separation, must take place either (1) before ligating step c), (2) after ligating step c), or (3) both before and after ligating step c), and wherein the first probe consists of a mixture of probes of different nucleic acid sequences, uniquely connected to a unique moiety which allows selectively separating the moiety form the reaction mixture, such that each unique nucleic acid sequence is attached to a unique moiety, whereby the selective separation of each unique moiety will allow the identification of the nucleic acid sequence of the target polynucleic acid.

42. A method for identifying a target polynucleic acid sequence in a reaction mixture, by detecting whether or not a label is present comprising:

a) selecting a first probe and a second probe, such that
  i) they are each complementary to a sufficient portion of the target to permit the formation of a hybrid,
  ii) the first probe is joined to a moiety which is a means for selectively separating the first probe from the reaction mixture,
  iii) the second probe is joined to a label or means for selectively attaching a label,
b) mixing the probes with the target polynucleic acid in such a manner that the probes will hybridize under high stringency conditions specifically to the target polynucleic acid,
c) adding a ligating reagent and sodium chloride, said sodium chloride being present in a concentration of greater than 200 mM and up to 1000 mM,
d) denaturing the hybridized probes and target polynucleic acid in the reaction mixture so that the probes will be separated from the target polynucleic acid,
e) separating the first probe from the reaction mixture, utilizing the moiety that permits selective separation, and
f) analyzing the selectively separated first probe to determine if the label, or means for attaching a label, of the second probe is present, whereby the identification of the target polynucleotide sequence is made, by correlating the presence or absence of label or means for attaching the label on the second probe with the presence or absence of the target polynucleotide, and analyzing the supernatant remaining after separation of the first probe to determine the amount of label present therein and, further, to determine the percent of hybridized labeled probe which has been ligated to said first probe, wherein a step for separating the hybridized probes and target, utilizing the moiety that permits selective separation, must take place either (1) before ligating step c), (2) after ligating step c), or (3) both before and after ligating step c), and wherein salt is present during the ligating step, such salt being present at a concentration of 200–1000 mM.

43. A method of claim 42 in which the salt concentration is 500–700 mM.

44. A method of claim 43 in which the salt concentration is approximately 600 mM.

45. A method of claim 42 in which said salt is KCl.

46. A method of claim 43 in which said salt is KCl.

47. A method of claim 44 in which said salt is KCl.

* * * * *